US010640550B2

(12) United States Patent
Takada et al.

(10) Patent No.: US 10,640,550 B2
(45) Date of Patent: May 5, 2020

(54) MONOCLONAL ANTIBODY NEUTRALIZING INFECTIVITY OF ALL EBOLA VIRUSES

(71) Applicant: NATIONAL UNIVERSITY CORPORATION HOKKAIDO UNIVERSITY, Hokkaido (JP)

(72) Inventors: Ayato Takada, Hokkaido (JP); Reiko Yoshida, Hokkaido (JP); Wakako Furuyama, Hokkaido (JP); Hiroko Miyamoto, Hokkaido (JP); Junki Maruyama, Hokkaido (JP); Shigeru Iida, Tokyo (JP); Shinya Ogawa, Tokyo (JP)

(73) Assignee: NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 48 days.

(21) Appl. No.: 15/753,035

(22) PCT Filed: Aug. 18, 2016

(86) PCT No.: PCT/JP2016/074146
§ 371 (c)(1),
(2) Date: Feb. 15, 2018

(87) PCT Pub. No.: WO2017/030172
PCT Pub. Date: Feb. 23, 2017

(65) Prior Publication Data
US 2018/0237503 A1 Aug. 23, 2018

(30) Foreign Application Priority Data

Aug. 19, 2015 (JP) ................................. 2015-161567

(51) Int. Cl.
| | | |
|---|---|---|
| C07K 16/10 | (2006.01) |
| A61P 31/14 | (2006.01) |
| G01N 33/569 | (2006.01) |
| C12N 5/10 | (2006.01) |
| A61K 39/395 | (2006.01) |
| C07K 1/16 | (2006.01) |
| C12N 15/02 | (2006.01) |
| C12N 15/09 | (2006.01) |

(52) U.S. Cl.
CPC ............ *C07K 16/10* (2013.01); *A61K 39/395* (2013.01); *A61P 31/14* (2018.01); *C07K 1/16* (2013.01); *C12N 5/10* (2013.01); *C12N 15/02* (2013.01); *C12N 15/09* (2013.01); *G01N 33/569* (2013.01); *C07K 2317/30* (2013.01); *C07K 2317/33* (2013.01); *C07K 2317/565* (2013.01); *C07K 2317/90* (2013.01)

(58) Field of Classification Search
None
See application file for complete search history.

(56) References Cited

U.S. PATENT DOCUMENTS

2012/0164153 A1* 6/2012 Dye ................. G01N 33/56983
424/147.1

OTHER PUBLICATIONS

Extended European Search Report dated Feb. 12, 2019 in corresponding European patent application No. 16837161.5.
Changula Katendi et al., "Mapping of conserved and species-specific antibody epitopes on th Ebola virus nucleoprotein", Virus Research, vol. 176, No. 1, May 20, 2013, pp. 83-90, XP028690301.
Marnie L. Fusco et al., "Protective mAbs and Cross-Reactive mAbs Raised by Immunization with Engineered Marburg Virus GPs", PLos pathogens, Jun. 26, 2015, pp. e1005016, XP055405438.
Oliver Reynard et al., "Characterization of a Novel Neutralizing Monoclonal Antibody Against Ebola Virus GP", Journal of Infectious Diseases. JID, vol. 212, No. suppl 2, Aug. 1, 2015, pp. S372-S378, XP055548982.
Z.A. Bornholdt et al., "Isolation of potent neutralizing antibodies from a survivor of the 2014 Ebola virus outbreak", Science, vol. 351, No. 6277, Feb. 18, 2016, pp. 1078-1083, XP055549012.
Wakako Furuyama et al., "Discovery of an antibody for pan-ebolavirus therapy", Scientific Reports, vol. 6, No. 1, Feb. 10, 2016, XP055549076.
Charles D. Murin et al., "Structural Basis of Pan-Ebolavirus Neutralization by an Antibody Targeting the Glycoprotein Fusion Loop", Cell Reports, vol. 24, No. 10, Sep. 1, 2018, pp. 2723-2732.e4, XP055548975.
International Search Report dated Nov. 15, 2016 in International (PCT) Application No. PCT/JP2016/074146, with English translation.
Written Opinion of the International Searching Authority dated Nov. 15, 2016 in International (PCT) Application No. PCT/JP2016/074146, with English translation.
Marzi et al., "Protective Efficacy of Neutralizing Monoclonal Antibodies in a Nonhuman Primate Model of Ebola Hemorrhagic Fever", PLoS One, 7(4):1-7 (2012) e36192.
Qiu et al., "Successful Treatment of Ebola Virus—Infected Cynomolgus Macaques with Monoclonal Antibodies", Science Translational Medicine, 4(138):1-11 (2012) 138ra81.
Dias et al., "A Shared Structural Solution for Neutralizing Ebolaviruses", Nat Struct Mol Biol, 18(12):1424-1427 (2012).
Qiu et al., "Reversion of advanced Ebola virus disease in nonhuman primates with ZMapp™", Nature, 514(7520):47-53 (2014).

* cited by examiner

*Primary Examiner* — Stacy B Chen
(74) *Attorney, Agent, or Firm* — Wenderoth, Lind & Ponack, L.L.P.

(57) ABSTRACT

There has been a need for a neutralizing monoclonal antibody which is useful for antibody therapy effective against ebolavirus.
The present invention provides a monoclonal antibody or an antigen-binding fragment thereof, which recognizes an internal fusion loop of ebolavirus GP and is capable of neutralizing the biological activity of ebolavirus.

17 Claims, 9 Drawing Sheets
Specification includes a Sequence Listing.

(C)
| | | SEQ ID NO: |
|---|---|---|
| Zaire(511-556) | CNPNLHYWTTQDEGAAIGLAWIPYFGPAAEGIYTEGLMHNQDGLIC | 1 |
| Sudan(511-556) | CNPNLHYWTAQEQHNAAGTAWIPYFGPAAEGIYTEGLMHNQNALVC | 2 |
| Bundibugyo(511-556) | CNPNLHYWTTQDEGAAIGLAWIPYFGPAAEGIYTEGLMHINQNGLIC | 3 |
| Tai Forest(511-556) | CNPNLHYWTALDEGAAIGLAWIPYFGPAAEGIYTEGIMHNQNGLIC | 4 |
| Reston(512-557) | CNPDLYYWTAVDEGAAVGLAWIPYFGPAAEGIYLEGVMHNQNGLIC | 5 |
| Zaire Escape[5/6] | CNPNLHYWTTQDEGAATRLAWIPYFGPAAEGIYTEGLMHNQDGLIC | 6 |
| Zaire Escape[1/6] | CNPNLHYWTTQDEGAAIELAWIPYFGPAAEGIYTEGLMHNQDGLIC | 7 |
| Reston Escape[2/6] | CNPDLYYWTAVDEGAAVELAWIPYFGPAAEGIYEGVMHNQNGLIC | 8 |
| Reston Escape[4/6] | CNPDLHYWTAADEGAAVGWAWIPYFGPAAEGIYEGVMHNQNGLIC | 9 |

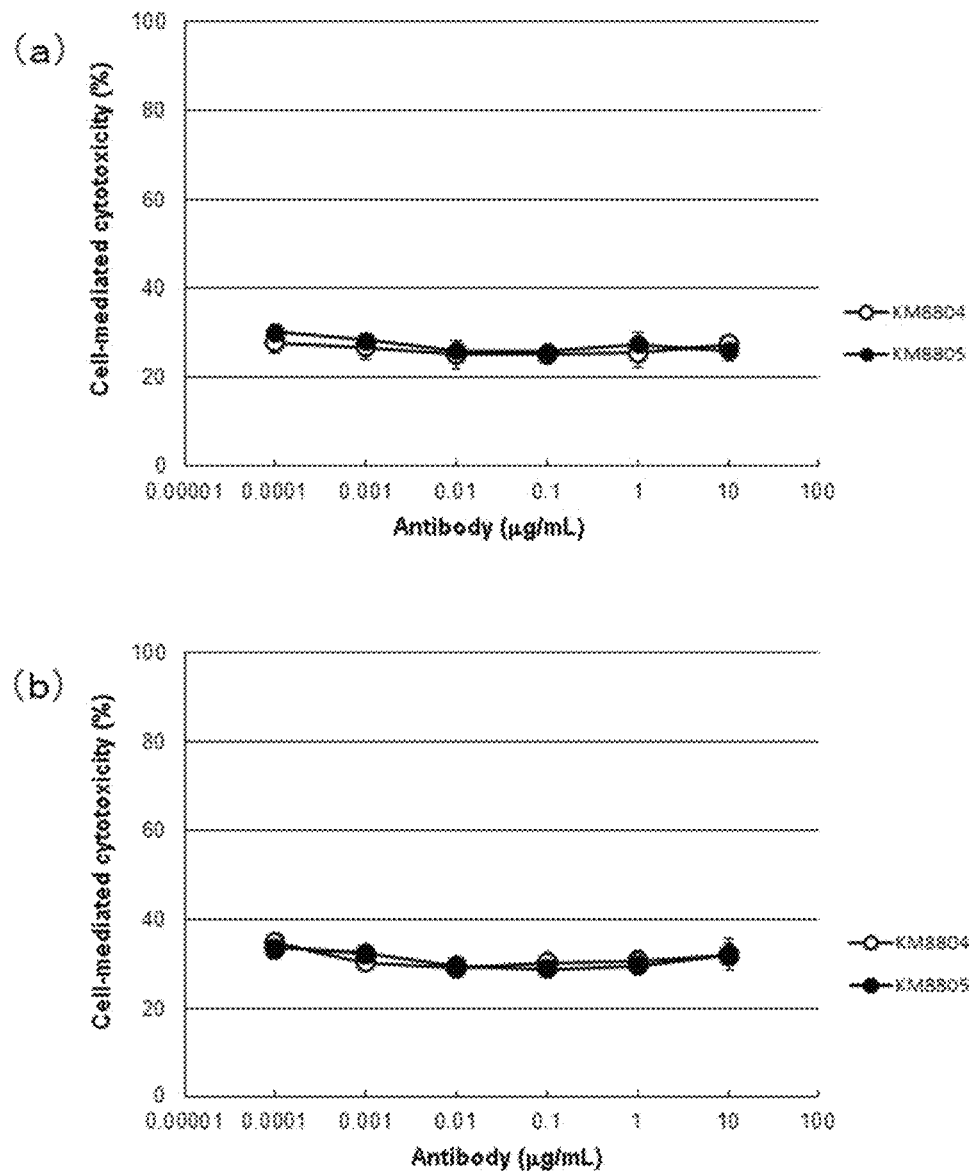

Fig. 8

Neutralizing activity against pseudotype viruses

SEQUENCE LISTING

<160> NUMBER OF SEQ ID NOS: 42

<210> SEQ ID NO 1
<211> LENGTH: 46
<212> TYPE: PRT
<213> ORGANISM: Zaire ebolavirus

<400> SEQUENCE: 1

Cys Asn Pro Asn Leu His Tyr Trp Thr Thr Gln Asp Glu Gly Ala Ala
1               5                   10                  15

Ile Gly Leu Ala Trp Ile Pro Tyr Phe Gly Pro Ala Ala Glu Gly Ile
            20                  25                  30

Tyr Ile Glu Gly Leu Met His Asn Gln Asp Gly Leu Ile Cys
        35                  40                  45

<210> SEQ ID NO 2
<211> LENGTH: 46
<212> TYPE: PRT
<213> ORGANISM: Sudan ebolavirus

<400> SEQUENCE: 2

Cys Asn Pro Asn Leu His Tyr Trp Thr Ala Gln Glu Gln His Asn Ala
1               5                   10                  15

Ala Gly Ile Ala Trp Ile Pro Tyr Phe Gly Pro Gly Ala Glu Gly Ile
            20                  25                  30

Tyr Thr Glu Gly Leu Met His Asn Gln Asn Ala Leu Val Cys
        35                  40                  45

<210> SEQ ID NO 3
<211> LENGTH: 46
<212> TYPE: PRT
<213> ORGANISM: Bundibugyo ebolavirus

<400> SEQUENCE: 3

Cys Asn Pro Asn Leu His Tyr Trp Thr Thr Gln Asp Glu Gly Ala Ala
1               5                   10                  15

Ile Gly Leu Ala Trp Ile Pro Tyr Phe Gly Pro Ala Ala Glu Gly Ile
            20                  25                  30

Tyr Thr Glu Gly Ile Met His Asn Gln Asn Gly Leu Ile Cys
        35                  40                  45

<210> SEQ ID NO 4
<211> LENGTH: 46
<212> TYPE: PRT
<213> ORGANISM: Tai Forest ebolavirus

<400> SEQUENCE: 4

Cys Asn Pro Asn Leu His Tyr Trp Thr Ala Leu Asp Glu Gly Ala Ala
1               5                   10                  15

Ile Gly Leu Ala Trp Ile Pro Tyr Phe Gly Pro Ala Ala Glu Gly Ile
            20                  25                  30

Tyr Thr Glu Gly Ile Met Glu Asn Gln Asn Gly Leu Ile Cys
        35                  40                  45

<210> SEQ ID NO 5
<211> LENGTH: 46
<212> TYPE: PRT
<213> ORGANISM: Reston ebolavirus

<400> SEQUENCE: 5

Cys Asn Pro Asp Leu Tyr Tyr Trp Thr Ala Val Asp Glu Gly Ala Ala

```
                1               5                   10                  15
Val Gly Leu Ala Trp Ile Pro Tyr Phe Gly Pro Ala Ala Glu Gly Ile
                20                  25                  30

Tyr Ile Glu Gly Val Met His Asn Gln Asn Gly Leu Ile Cys
        35                  40                  45

<210> SEQ ID NO 6
<211> LENGTH: 46
<212> TYPE: PRT
<213> ORGANISM: Zaire ebolavirus Escape Mutant

<400> SEQUENCE: 6

Cys Asn Pro Asn Leu His Tyr Trp Thr Thr Gln Asp Glu Gly Ala Ala
1               5                   10                  15

Ile Arg Leu Ala Trp Ile Pro Tyr Phe Gly Pro Ala Ala Glu Gly Ile
                20                  25                  30

Tyr Ile Glu Gly Leu Met His Asn Gln Asp Gly Leu Ile Cys
        35                  40                  45

<210> SEQ ID NO 7
<211> LENGTH: 46
<212> TYPE: PRT
<213> ORGANISM: Zaire ebolavirus Escape Mutant

<400> SEQUENCE: 7

Cys Asn Pro Asn Leu His Tyr Trp Thr Thr Gln Asp Glu Gly Ala Ala
1               5                   10                  15

Ile Glu Leu Ala Trp Ile Pro Tyr Phe Gly Pro Ala Ala Glu Gly Ile
                20                  25                  30

Tyr Ile Glu Gly Leu Met His Asn Gln Asp Gly Leu Ile Cys
        35                  40                  45

<210> SEQ ID NO 8
<211> LENGTH: 46
<212> TYPE: PRT
<213> ORGANISM: Reston ebolavirus Escape Mutant

<400> SEQUENCE: 8

Cys Asn Pro Asp Leu Tyr Tyr Trp Thr Ala Val Asp Glu Gly Ala Ala
1               5                   10                  15

Val Glu Leu Ala Trp Ile Pro Tyr Phe Gly Pro Ala Ala Glu Gly Ile
                20                  25                  30

Tyr Ile Glu Gly Val Met His Asn Gln Asn Gly Leu Ile Cys
        35                  40                  45

<210> SEQ ID NO 9
<211> LENGTH: 46
<212> TYPE: PRT
<213> ORGANISM: Reston ebolavirus Escape Mutant

<400> SEQUENCE: 9

Cys Asn Pro Asp Leu Tyr Tyr Trp Thr Ala Val Asp Glu Gly Ala Ala
1               5                   10                  15

Val Gly Leu Ala Trp Ile Pro Tyr Phe Gly Pro Ala Ala Glu Gly Ile
                20                  25                  30

Tyr Ile Glu Gly Val Met His Asn Gln Asn Gly Leu Ile Cys
        35                  40                  45

<210> SEQ ID NO 10
<211> LENGTH: 108
```

```
<212> TYPE: PRT
<213> ORGANISM: Mus musculus

<400> SEQUENCE: 10

Asp Ile Val Val Thr Gln Ser His Lys Phe Met Ser Thr Ser Val Gly
1               5                   10                  15

Asp Arg Val Ser Ile Thr Cys Lys Ala Ser Gln Asp Val Ser Val Ala
            20                  25                  30

Val Ala Trp Tyr Gln Gln Lys Thr Gly Gln Ser Pro Lys Leu Leu Ile
        35                  40                  45

Tyr Ser Ala Ser Tyr Arg Ile Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Met Ala Val Tyr Tyr Cys Gln Gln His Tyr Ser Thr Pro Pro
                85                  90                  95

Trp Thr Phe Gly Gly Gly Thr Lys Leu Glu Ile Lys
            100                 105

<210> SEQ ID NO 11
<211> LENGTH: 118
<212> TYPE: PRT
<213> ORGANISM: Mus musculus

<400> SEQUENCE: 11

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Arg Asn Gly Arg Thr Asp Phe Ser Glu Lys Phe
    50                  55                  60

Lys Ser Lys Ala Thr Leu Thr Val Asp Thr Ser Ser Ser Thr Ala Phe
65                  70                  75                  80

Ile Gln Leu Ser Ser Leu Thr Ser Glu Asp Ser Ala Val Tyr Tyr Cys
                85                  90                  95

Ala Arg Trp Gly Tyr Tyr Gly Ser Cys Asp Tyr Trp Gly Gln Gly Thr
            100                 105                 110

Ala Leu Thr Val Ser Ser
        115

<210> SEQ ID NO 12
<211> LENGTH: 11
<212> TYPE: PRT
<213> ORGANISM: Mus musculus

<400> SEQUENCE: 12

Lys Ala Ser Gln Asp Val Ser Val Ala Val Ala
1               5                   10

<210> SEQ ID NO 13
<211> LENGTH: 7
<212> TYPE: PRT
<213> ORGANISM: Mus musculus

<400> SEQUENCE: 13

Ser Ala Ser Tyr Arg Ile Thr
1               5
```

<210> SEQ ID NO 14
<211> LENGTH: 10
<212> TYPE: PRT
<213> ORGANISM: Mus musculus

<400> SEQUENCE: 14

Gln Gln His Tyr Ser Thr Pro Pro Trp Thr
1               5                   10

<210> SEQ ID NO 15
<211> LENGTH: 5
<212> TYPE: PRT
<213> ORGANISM: Mus musculus

<400> SEQUENCE: 15

Ser Tyr Trp Met His
1               5

<210> SEQ ID NO 16
<211> LENGTH: 17
<212> TYPE: PRT
<213> ORGANISM: Mus musculus

<400> SEQUENCE: 16

Glu Ile Asn Pro Arg Asn Gly Arg Thr Asp Phe Ser Glu Lys Phe Lys
1               5                   10                  15

Ser

<210> SEQ ID NO 17
<211> LENGTH: 9
<212> TYPE: PRT
<213> ORGANISM: Mus musculus

<400> SEQUENCE: 17

Trp Gly Tyr Tyr Gly Ser Cys Asp Tyr
1               5

<210> SEQ ID NO 18
<211> LENGTH: 10
<212> TYPE: PRT
<213> ORGANISM: Mus musculus

<400> SEQUENCE: 18

Gly Tyr Thr Phe Thr Ser Tyr Trp Met His
1               5                   10

<210> SEQ ID NO 19
<211> LENGTH: 10
<212> TYPE: PRT
<213> ORGANISM: Mus musculus

<400> SEQUENCE: 19

Glu Ile Asn Pro Arg Asn Gly Arg Thr Asp
1               5                   10

<210> SEQ ID NO 20
<211> LENGTH: 9
<212> TYPE: PRT
<213> ORGANISM: Mus musculus

<400> SEQUENCE: 20

Trp Gly Tyr Tyr Gly Ser Cys Asp Tyr
1               5

<210> SEQ ID NO 21
<211> LENGTH: 7
<212> TYPE: PRT
<213> ORGANISM: Mus musculus

<400> SEQUENCE: 21

Gly Tyr Thr Phe Thr Ser Tyr
1               5

<210> SEQ ID NO 22
<211> LENGTH: 6
<212> TYPE: PRT
<213> ORGANISM: Mus musculus

<400> SEQUENCE: 22

Asn Pro Arg Asn Gly Arg
1               5

<210> SEQ ID NO 23
<211> LENGTH: 9
<212> TYPE: PRT
<213> ORGANISM: Mus musculus

<400> SEQUENCE: 23

Trp Gly Tyr Tyr Gly Ser Cys Asp Tyr
1               5

<210> SEQ ID NO 24
<211> LENGTH: 215
<212> TYPE: PRT
<213> ORGANISM: Mus musculus

<400> SEQUENCE: 24

Asp Ile Val Val Thr Gln Ser His Lys Phe Met Ser Thr Ser Val Gly
1               5                   10                  15

Asp Arg Val Ser Ile Thr Cys Lys Ala Ser Gln Asp Val Ser Val Ala
            20                  25                  30

Val Ala Trp Tyr Gln Gln Lys Thr Gly Gln Ser Pro Lys Leu Leu Ile
        35                  40                  45

Tyr Ser Ala Ser Tyr Arg Ile Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Met Ala Val Tyr Tyr Cys Gln Gln His Tyr Ser Thr Pro Pro
                85                  90                  95

Trp Thr Phe Gly Gly Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys

```
              195                 200                 205

Ser Phe Asn Arg Asn Glu Cys
    210                 215

<210> SEQ ID NO 25
<211> LENGTH: 442
<212> TYPE: PRT
<213> ORGANISM: Mus musculus

<400> SEQUENCE: 25

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Arg Asn Gly Arg Thr Asp Phe Ser Glu Lys Phe
    50                  55                  60

Lys Ser Lys Ala Thr Leu Thr Val Asp Thr Ser Ser Ser Thr Ala Phe
65                  70                  75                  80

Ile Gln Leu Ser Ser Leu Thr Ser Glu Asp Ser Ala Val Tyr Tyr Cys
                85                  90                  95

Ala Arg Trp Gly Tyr Tyr Gly Ser Cys Asp Tyr Trp Gly Gln Gly Thr
            100                 105                 110

Ala Leu Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350
```

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440

<210> SEQ ID NO 26
<211> LENGTH: 65
<212> TYPE: DNA
<213> ORGANISM: Artificial
<220> FEATURE:
<223> OTHER INFORMATION: Synthetic

<400> SEQUENCE: 26
cagcttcctg cttatttcgg cctcagtcat aatgtccaga ggagacattg tggtgaccca    60
gtctc                                                                65

<210> SEQ ID NO 27
<211> LENGTH: 36
<212> TYPE: DNA
<213> ORGANISM: Artificial
<220> FEATURE:
<223> OTHER INFORMATION: Synthetic

<400> SEQUENCE: 27
gtgcagccac cgtacgtttg atttccagct tggtgc                               36

<210> SEQ ID NO 28
<211> LENGTH: 70
<212> TYPE: DNA
<213> ORGANISM: Artificial
<220> FEATURE:
<223> OTHER INFORMATION: Synthetic

<400> SEQUENCE: 28
gtcagatcgc gtcgacgcct cctcaaaatg catttcaag tgcagatttt cagcttcctg      60
cttatttcgg                                                            70

<210> SEQ ID NO 29
<211> LENGTH: 19
<212> TYPE: DNA
<213> ORGANISM: Artificial
<220> FEATURE:
<223> OTHER INFORMATION: Synthetic

<400> SEQUENCE: 29
gtgcagccac cgtacgttt                                                  19

<210> SEQ ID NO 30
<211> LENGTH: 24
<212> TYPE: DNA
<213> ORGANISM: Artificial
<220> FEATURE:
<223> OTHER INFORMATION: Synthetic

<400> SEQUENCE: 30
agagattaat cctaggaacg gtcg                    24

<210> SEQ ID NO 31
<211> LENGTH: 27
<212> TYPE: DNA
<213> ORGANISM: Artificial
<220> FEATURE:
<223> OTHER INFORMATION: Synthetic

<400> SEQUENCE: 31
gtagtcagcg ctaccgtaat atcccca                 27

<210> SEQ ID NO 32
<211> LENGTH: 27
<212> TYPE: DNA
<213> ORGANISM: Artificial
<220> FEATURE:
<223> OTHER INFORMATION: Synthetic

<400> SEQUENCE: 32
ggtagcgctg actactgggg ccagggc                 27

<210> SEQ ID NO 33
<211> LENGTH: 18
<212> TYPE: DNA
<213> ORGANISM: Artificial
<220> FEATURE:
<223> OTHER INFORMATION: Synthetic

<400> SEQUENCE: 33
gaagaccgat gggcccctt                          18

<210> SEQ ID NO 34
<211> LENGTH: 27
<212> TYPE: DNA
<213> ORGANISM: Artificial
<220> FEATURE:
<223> OTHER INFORMATION: Synthetic

<400> SEQUENCE: 34
gtagtcgctg ctaccgtaat atcccca                 27

<210> SEQ ID NO 35
<211> LENGTH: 27
<212> TYPE: DNA
<213> ORGANISM: Artificial
<220> FEATURE:
<223> OTHER INFORMATION: Synthetic

<400> SEQUENCE: 35
ggtagcagcg actactgggg ccagggc                 27

<210> SEQ ID NO 36
<211> LENGTH: 108
<212> TYPE: PRT
<213> ORGANISM: Artificial
<220> FEATURE:
<223> OTHER INFORMATION: Recombinant

<400> SEQUENCE: 36

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Val Ala
            20                  25                  30

Val Ala Trp Tyr Gln Gln Lys Pro Gly Gln Pro Pro Lys Leu Leu Ile
                35                  40                  45

Tyr Ser Ala Ser Tyr Arg Ile Thr Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Tyr Ser Thr Pro Pro
                85                  90                  95

Trp Thr Phe Gly Gln Gly Thr Lys Val Glu Ile Lys
            100                 105

<210> SEQ ID NO 37
<211> LENGTH: 108
<212> TYPE: PRT
<213> ORGANISM: Artificial
<220> FEATURE:
<223> OTHER INFORMATION: Recombinant

<400> SEQUENCE: 37

Asp Ile Val Leu Thr Gln Ser Pro Ser Phe Leu Ser Ala Ser Val Gly
1               5                   10                  15

Asp Arg Val Thr Ile Thr Cys Lys Ala Ser Gln Asp Val Ser Val Ala
                20                  25                  30

Val Ala Trp Tyr Gln Gln Lys Pro Gly Lys Ala Pro Lys Leu Leu Ile
                35                  40                  45

Tyr Ser Ala Ser Tyr Arg Ile Thr Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Ala Tyr Tyr Cys Gln Gln His Tyr Ser Thr Pro Pro
                85                  90                  95

Trp Thr Phe Gly Gly Gly Thr Lys Leu Glu Ile Lys
            100                 105

<210> SEQ ID NO 38
<211> LENGTH: 118
<212> TYPE: PRT
<213> ORGANISM: Artificial
<220> FEATURE:
<223> OTHER INFORMATION: Recombinant

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
                35                  40                  45

Gly Glu Ile Asn Pro Arg Asn Gly Arg Thr Asp Phe Ser Glu Lys Phe
        50                  55                  60

Lys Ser Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Tyr Tyr Gly Ser Cys Asp Tyr Trp Gly Gln Gly Thr
            100                 105                 110

Leu Val Thr Val Ser Ser
            115

```
<210> SEQ ID NO 39
<211> LENGTH: 118
<212> TYPE: PRT
<213> ORGANISM: Artificial
<220> FEATURE:
<223> OTHER INFORMATION: Recombinant

<400> SEQUENCE: 39

Glu Val Gln Leu Val Gln Ser Gly Gly Glu Val Arg Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Val
        35                  40                  45

Gly Glu Ile Asn Pro Arg Asn Gly Arg Thr Asp Phe Ser Glu Lys Phe
    50                  55                  60

Lys Ser Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Tyr Tyr Gly Ser Cys Asp Tyr Trp Gly Gln Gly Thr
            100                 105                 110

Leu Val Thr Val Ser Ser
        115

<210> SEQ ID NO 40
<211> LENGTH: 9
<212> TYPE: PRT
<213> ORGANISM: Artificial
<220> FEATURE:
<223> OTHER INFORMATION: HCDR3 (Ala)

<400> SEQUENCE: 40

Trp Gly Tyr Tyr Gly Ser Ala Asp Tyr
1               5

<210> SEQ ID NO 41
<211> LENGTH: 9
<212> TYPE: PRT
<213> ORGANISM: Artificial
<220> FEATURE:
<223> OTHER INFORMATION: HCDR3 (Ser)

<400> SEQUENCE: 41

Trp Gly Tyr Tyr Gly Ser Ser Asp Tyr
1               5

<210> SEQ ID NO 42
<211> LENGTH: 118
<212> TYPE: PRT
<213> ORGANISM: Artificial Sequence
<220> FEATURE:
<223> OTHER INFORMATION: Artificial Recombinant Protein

<400> SEQUENCE: 42

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45
```

```
Gly Glu Ile Asn Pro Arg Asn Gly Arg Thr Asp Phe Ser Glu Lys Phe
    50              55                  60

Lys Ser Lys Ala Thr Leu Thr Val Asp Thr Ser Ser Thr Ala Phe
65              70              75              80

Ile Gln Leu Ser Ser Leu Thr Ser Glu Asp Ser Ala Val Tyr Tyr Cys
            85              90                  95

Ala Arg Trp Gly Tyr Gly Ser Ser Asp Tyr Trp Gly Gln Gly Thr
            100             105             110

Ala Leu Thr Val Ser Ser
            115
```

US 10,640,550 B2

MONOCLONAL ANTIBODY NEUTRALIZING INFECTIVITY OF ALL EBOLA VIRUSES

TECHNICAL FIELD

The present invention relates to a monoclonal antibody recognizing ebolavirus.

BACKGROUND ART

Viruses of the family Filoviridae, i.e., filoviruses are pathogens which infect primates including humans to cause serious hemorrhagic fever with an extremely high fatality rate in the infected primates. Mass infection with filoviruses is currently limited to Africa, but there is no denying the possibility that mass infection will also break out in any other regions in the future due to recent advances in the worldwide transportation network. In addition, there is currently no commercially available prophylactic or therapeutic agent which is effective against filovirus infection.

In the family Filoviridae, only two genera, Marburgvirus and Ebolavirus, have been identified. Further, in the genus Ebolavirus, the following five species have been identified: Zaire ebolavirus, Sudan ebolavirus, Tai Forest ebolavirus, Bundibugyo ebolavirus and Reston ebolavirus.

Ebola virus disease (EVD) caused by infection with viruses of the genus Ebolavirus, i.e., ebolaviruses has an average fatality rate of about 50%, and the fatality rate in the past epidemic is in the range of 25% to 90%. The incubation period from infection with ebolaviruses to development of EVD is 2 to 21 days. Early symptoms of EVD are fatigue fever, myalgia, headache and sore throat, which are followed by vomiting, diarrhea, exanthema, renal and hepatic dysfunction, external hemorrhage, and other symptoms.

Recently, studies in monkey infection models have demonstrated that passive immunization with monoclonal antibodies neutralizing ebolavirus infectivity is effective for treatment of EVD (Non-patent Document 1 and Non-patent Document 2). During the epidemic caused in West African in 2014, the infected patients received antibody therapy which had not been approved as a drug. However, monoclonal antibodies hitherto developed exert their effect only on the treatment of EVD caused by Zaire ebolavirus among the five ebolavirus species.

On the other hand, EVD caused by Sudan ebolavirus and Bundibugyo ebolavirus among the five ebolavirus species have also occurred frequently since 2000.

PRIOR AN DOCUMENTS

Non-Patent Documents

Non-patent Document 1: Marzi A, et al., Protective efficacy of neutralizing monoclonal antibodies in a nonhuman primate model of Ebola hemorrhagic fever. PLoS ONE 7(4): e36192, 2012

Non-patent Document 2: Qiu X, et al., Successful treatment of ebola virus-infected cynomolgus macaques with monoclonal antibodies. Sci Transl Med 4(138): 138ra81, 2012

SUMMARY OF THE INVENTION

Problem to be Solved by the Invention

Under such circumstances as described above, there has been a demand for a neutralizing monoclonal antibody which is useful for antibody therapy effective against ebolavirus.

Means to Solve the Problem

As a result of repeating extensive and intensive efforts to solve the problem stated above, the inventors of the present invention have created a monoclonal antibody, 6D6, which recognizes an internal fusion loop on glycoprotein GP in all the five ebolavirus species and efficiently neutralizes ebolavirus infectivity, thereby completing the present invention.

Namely, the present invention is as follows.

<1>
A monoclonal antibody or an antigen-binding fragment thereof, which recognizes an internal fusion loop of surface glycoprotein (hereinafter abbreviated as GP) of ebolavirus and is capable of neutralizing the biological activity of the ebolavirus.

<2>
The monoclonal antibody or antigen-binding fragment thereof according to <1> above, wherein the ebolavirus whose GP internal fusion loop is to be recognized comprises all of the following ebolaviruses: Zaire ebolavirus, Sudan ebolavirus, Bundibugyo ebolavirus, Reston ebolavirus and Tai Forest ebolavirus.

<3>
The monoclonal antibody or antigen-binding fragment thereof according to <2> above, wherein the GP internal fusion loop to be recognized comprises all of: the one consisting of the amino acid sequence of SEQ ID NO: 1; the one consisting of the amino acid sequence of SEQ 1D NO: 2; the one consisting of the amino acid sequence of SEQ 1D NO: 3; the one consisting of the amino acid sequence of SEQ ID NO: 4; and the one consisting of the amino acid sequence of SEQ ID NO: 5.

<4>
The monoclonal antibody or antigen-binding fragment thereof according to any one of <1> to <3> above, which comprises:
a light chain variable region comprising:
light chain CDR1 consisting of an amino acid sequence selected from the group consisting of the amino acid sequence of SEQ ID NO: 12; an amino acid sequence mutated to have deletion, substitution, insertion and/or addition of one to several amino acid residues in the amino acid sequence of SEQ ID NO: 12; and an amino acid sequence having an identity of 90% or more with the amino acid sequence of SEQ ID NO: 12,
light chain CDR2 consisting of an amino acid sequence selected from the group consisting of the amino acid sequence of SEQ ID NO: 13; an amino acid sequence mutated to have deletion, substitution, insertion and/or addition of one to several amino acid residues in the amino acid sequence of SEQ ID NO: 13; and an amino acid sequence having an identity of 90% or more with the amino acid sequence of SEQ ID NO: 13, and
light chain CDR3 consisting of an amino acid sequence selected from the group consisting of the amino acid sequence of SEQ ID NO: 14; an amino acid sequence mutated to have deletion, substitution, insertion and/or addition of one to several amino acid residues in the amino acid sequence of SEQ ID NO: 14; and an amino acid sequence having an identity of 90% or more with the amino acid sequence of SEQ ID NO: 14; and a heavy chain variable region comprising:

heavy chain CDR1 consisting of an amino acid sequence selected from the group consisting of the amino acid sequence of SEQ ID NO: 15; an amino acid sequence mutated to have deletion, substitution, insertion and/or addition of one to several amino acid residues in the amino acid sequence of SEQ ID NO: 15; and an amino acid sequence having an identity of 90% or more with the amino acid sequence of SEQ ID NO: 15, heavy chain CDR2 consisting of an amino acid sequence selected from the group consisting of the amino acid sequence of SEQ ID NO: 16; an amino acid sequence mutated to have deletion, substitution, insertion and/or addition of one to several amino acid residues in the amino acid sequence of SEQ ID NO: 16; and an amino acid sequence having an identity of 90% or more with the amino acid sequence of SEQ ID NO: 16, and heavy chain CDR3 consisting of an amino acid sequence selected from the group consisting of the amino acid sequence of SEQ ID NO: 17; an amino acid sequence mutated to have deletion, substitution, insertion and/or addition of one to several amino acid residues in the amino acid sequence of SEQ ID NO: 17; and an amino acid sequence having an identity of 90% or more with the amino acid sequence of SEQ ID NO: 17.

<5>

The monoclonal antibody or antigen-binding fragment thereof according to any one of <1> to <3> above, which comprises:

a light chain variable region comprising:

light chain CDR1 consisting of an amino acid sequence selected from the group consisting of the amino acid sequence of SEQ ID NO: 12; an amino acid sequence mutated to have deletion, substitution, insertion and/or addition of one to several amino acid residues in the amino acid sequence of SEQ ID NO: 12; and an amino acid sequence having an identity of 90% or more with the amino acid sequence of SEQ ID NO: 12, light chain CDR2 consisting of an amino acid sequence selected from the group consisting of the amino acid sequence of SEQ ID NO: 13; an amino acid sequence mutated to have deletion, substitution, insertion and/or addition of one to several amino acid residues in the amino acid sequence of SEQ ID NO: 13; and an amino acid sequence having an identity of 90% or more with the amino acid sequence of SEQ ID NO: 13, and light chain CDR3 consisting of an amino acid sequence selected from the group consisting of the amino acid sequence of SEQ ID NO: 14; an amino acid sequence mutated to have deletion, substitution, insertion and/or addition of one to several amino acid residues in the amino acid sequence of SEQ ID NO: 14; and an amino acid sequence having an identity of 90% or more with the amino acid sequence of SEQ ID NO: 14; and a heavy chain variable region comprising:

heavy chain CDR1 consisting of an amino acid sequence selected from the group consisting of the amino acid sequence of SEQ ID NO: 18; an amino acid sequence mutated to have deletion, substitution, insertion and/or addition of one to several amino acid residues in the amino acid sequence of SEQ ID NO: 18; and an amino acid sequence having an identity of 90% or more with the amino acid sequence of SEQ ID NO: 18, heavy chain CDR2 consisting of an amino acid sequence selected from the group consisting of the amino acid sequence of SEQ ID NO: 19; an amino acid sequence mutated to have deletion, substitution, insertion and/or addition of one to several amino acid residues in the amino acid sequence of SEQ ID NO: 19; and an amino acid sequence having an identity of 90% or more with the amino acid sequence of SEQ ID NO: 19, and heavy chain CDR3 consisting of an amino acid sequence selected from the group consisting of the amino acid sequence of SEQ ID NO: 20; an amino acid sequence mutated to have deletion, substitution, insertion and/or addition of one to several amino acid residues in the amino acid sequence of SEQ ID NO: 20, and an amino acid sequence having an identity of 90% or more with the amino acid sequence of SEQ ID NO: 20.

<6>

The monoclonal antibody or antigen-binding fragment thereof according to any one of <1> to <3> above, which comprises:

a light chain variable region comprising:

light chain CDR1 consisting of an amino acid sequence selected from the group consisting of the amino acid sequence of SEQ ID NO: 12; an amino acid sequence mutated to have deletion, substitution, insertion and/or addition of one to several amino acid residues in the amino acid sequence of SEQ ID NO: 12; and an amino acid sequence having an identity of 90% or more with the amino acid sequence of SEQ ID NO: 12, light chain CDR2 consisting of an amino acid sequence selected from the group consisting of the amino acid sequence of SEQ ID NO: 13; an amino acid sequence mutated to have deletion, substitution, insertion and/or addition of one to several amino acid residues in the amino acid sequence of SEQ ID NO: 13; and an amino acid sequence having an identity of 90% or more with the amino acid sequence of SEQ ID NO: 13, and light chain CDR3 consisting of an amino acid sequence selected from the group consisting of the amino acid sequence of SEQ ID NO: 14; an amino acid sequence mutated to have deletion, substitution, insertion and/or addition of one to several amino acid residues in the amino acid sequence of SEQ ID NO: 14; and an amino acid sequence having an identity of 90% or more with the amino acid sequence of SEQ ID NO: 14; and a heavy chain variable region comprising:

heavy chain CDR1 consisting of an amino acid sequence selected from the group consisting of the amino acid sequence of SEQ ID NO: 21; an amino acid sequence mutated to have deletion, substitution, insertion and/or addition of one to several amino acid residues in the amino acid sequence of SEQ ID NO: 21; and an amino acid sequence having an identity of 90% or more with the amino acid sequence of SEQ ID NO: 21, heavy chain CDR2 consisting of an amino acid sequence selected from the group consisting of the amino acid sequence of SEQ ID NO: 22; an amino acid sequence mutated to have deletion, substitution, insertion and/or addition of one to several amino acid residues in the amino acid sequence of SEQ ID NO: 22; and an amino acid sequence having an identity of 90% or more with the amino acid sequence of SEQ ID NO: 22, and heavy chain CDR3 consisting of an amino acid sequence selected from the group consisting of the amino acid sequence of SEQ ID NO: 23; an amino acid sequence mutated to have deletion, substitution, insertion and/or addition of one to several amino acid residues in the amino acid sequence of SEQ ID NO: 23; and an amino acid sequence having an identity of 90% or more with the amino acid sequence of SEQ ID NO: 23.

<7>

The monoclonal antibody or antigen-binding fragment thereof according to <4> above, which is any one selected from:

a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and
a heavy chain variable region comprising heavy chain CDR1 consisting of the amino acid sequence of SEQ ID NO: 15, heavy chain CDR2 consisting of the amino acid sequence of SEQ ID NO: 16, and heavy chain CDR3 consisting of the amino acid sequence of SEQ ID NO: 17;

a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and
a heavy chain variable region comprising heavy chain CDR1 consisting of the amino acid sequence of SEQ ID NO: 15, heavy chain CDR2 consisting of the amino acid sequence of SEQ ID NO: 16, and heavy chain CDR3 consisting of the amino acid sequence of SEQ ID NO: 40; and a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and
a heavy chain variable region comprising heavy chain CDR1 consisting of the amino acid sequence of SEQ ID NO: 15, heavy chain CDR2 consisting of the amino acid sequence of SEQ ID NO: 16, and heavy chain CDR3 consisting of the amino acid sequence of SEQ ID NO: 41.

<8>

The monoclonal antibody or antigen-binding fragment thereof according to <5> above, which is any one selected from:

a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and
a heavy chain variable region comprising heavy chain CDR1 consisting of the amino acid sequence of SEQ ID NO: 18, heavy chain CDR2 consisting of the amino acid sequence of SEQ ID NO: 19, and heavy chain CDR3 consisting of the amino acid sequence of SEQ ID NO: 20;

a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and
a heavy chain variable region comprising heavy chain CDR1 consisting of the amino acid sequence of SEQ ID NO: 18, heavy chain CDR2 consisting of the amino acid sequence of SEQ ID NO: 19, and heavy chain CDR3 consisting of the amino acid sequence of SEQ ID NO: 40; and a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and
a heavy chain variable region comprising heavy chain CDR1 consisting of the amino acid sequence of SEQ ID NO: 18, heavy chain CDR2 consisting of the amino acid sequence of SEQ ID NO: 19, and heavy chain CDR3 consisting of the amino acid sequence of SEQ ID NO: 41.

<9>

The monoclonal antibody or antigen-binding fragment thereof according to <6> above, which is any one selected from:

a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and
a heavy chain variable region comprising heavy chain CDR1 consisting of the amino acid sequence of SEQ ID NO: 21, heavy chain CDR2 consisting of the amino acid sequence of SEQ ID NO: 22, and heavy chain CDR3 consisting of the amino acid sequence of SEQ ID NO: 23;

a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and
a heavy chain variable region comprising heavy chain CDR1 consisting of the amino acid sequence of SEQ ID NO: 21, heavy chain CDR2 consisting of the amino acid sequence of SEQ ID NO: 22, and heavy chain CDR3 consisting of the amino acid sequence of SEQ ID NO: 40; and a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and
a heavy chain variable region comprising heavy chain CDR1 consisting of the amino acid sequence of SEQ ID NO: 21, heavy chain CDR2 consisting of the amino acid sequence of SEQ ID NO: 22, and heavy chain CDR3 consisting of the amino acid sequence of SEQ ID NO: 41.

<10>

The monoclonal antibody or antigen-binding fragment thereof according to any one of <1> to <9> above, which comprises:

a light chain variable region consisting of an amino acid sequence selected from the group consisting of the amino acid sequence of SEQ ID NO: 10; an amino acid sequence mutated to have deletion, substitution, insertion and/or addition of one to several amino acid residues in the amino acid sequence of SEQ ID NO: 10; and an amino acid sequence having an identity of 90a % a or more with the amino acid sequence of SEQ ID NO: 10; and a heavy chain variable region consisting of an amino acid sequence selected from the group consisting of the amino acid sequence of SEQ ID NO: 11; an amino acid sequence mutated to have deletion, substitution, insertion and/or addition of one to several amino acid residues in the amino acid sequence of SEQ ID NO: 11; and an amino acid sequence having an identity of 90% or more with the amino acid sequence of SEQ ID NO: 11.

<11>

The monoclonal antibody or antigen-binding fragment thereof according to <10> above, which comprises:

a light chain variable region consisting of the amino acid sequence of SEQ ID NO: 10; and a heavy chain variable region consisting of the amino acid sequence of SEQ II) NO: 11.

<12>

The monoclonal antibody or antigen-binding fragment thereof according to any one of <1> to <11> above, which is a chimeric antibody or a humanized antibody.

<13>

The monoclonal antibody or antigen-binding fragment thereof according to any one of claims 1 to 12, which has antibody-dependent cell-mediated cytotoxicity.

<14>

An isolated nucleic acid molecule, which encodes the monoclonal antibody or antigen-binding fragment thereof according to any one of <1> to <13> above.

<15>

An expression vector, which comprises the nucleic acid molecule according to <14> above.

<16>

A hybridoma cell or a transformed cell, which comprises the nucleic acid molecule according to <14> above.

<17>

A diagnostic reagent for ebolavirus infection, which comprises the monoclonal antibody or antigen-binding fragment thereof according to any one of <1> to <13> above.

<18>

A medicament, which comprises the monoclonal antibody or antigen-binding fragment thereof according to any one of <1> to <13> above.

<19>

The medicament according to <18> above, which is a prophylactic or therapeutic agent for Ebola virus disease.

<20>

A method for producing the antibody or antigen-binding fragment thereof according to any one of <1> to <13> above, which comprises the steps of culturing the hybridoma or transformed cell according to <16> above in a medium to produce and accumulate the antibody in the culture supernatant, and collecting and purifying the antibody.

Effects of the Invention

The monoclonal antibody of the present invention recognizes ebolavirus responsible for causing Ebola virus disease and is capable of canceling (neutralizing) the biological activity of the ebolavirus. In a preferred embodiment, the monoclonal antibody of the present invention is useful as a diagnostic reagent for symptoms of Ebola virus disease and as a medicament including a prophylactic or therapeutic agent for Ebola virus disease.

BRIEF DESCRIPTION OF THE DRAWINGS

FIG. 1 shows pseudotype vesicular stomatitis viruses (VSVs) having surface glycoprotein (GP) of ebolavirus prepared in the Examples. (A) Replication-incompetent pseudotype VSV particle. (B) Replication-competent pseudotype VSV particle.

FIG. 2 presents a graph showing the cross-neutralizing activity of mouse monoclonal antibody 6D6.

FIG. 3 shows a deduced epitope (an internal fusion loop consisting of an amino acid sequence located at positions 511 to 556 (an amino acid sequence located at positions 512 to 557 in Reston)) for mouse monoclonal antibody 6D6. (A) Each arrow indicates a mutation site observed in a Zaire GP escape mutant. (B) Schematic view of the Class I pre-fusion Zaire GP internal fusion loop (source: Lee J E, et al., Nature. 2008, 454, 177-82). (C) Amino acid sequences of the respective epitopes.

FIG. 5-1 shows the neutralizing activity of mouse monoclonal antibody 6D6, 6D6 chimeric antibody, CDR-modified 6D6 chimeric antibody (Ser) and CDR-modified 6D6 chimeric antibody (Ala) against various ebolaviruses. Neutralizing activity against (a) pseudotype vesicular stomatitis virus (VSV) used as a negative control, (b) Zaire ebolavirus, (c) Sudan ebolavirus, (d) Tai Forest ebolavirus, (e) Bundibugyo ebolavirus and (f) Reston ebolavirus is shown. In each graph, the horizontal axis represents antibody concentration and the vertical axis represents infectivity (%).

FIG. 5-2 (continued from FIG. 5-1)

FIG. 6 shows the results obtained when anti-DNP antibodies KM8804 and KM8805 were measured for their cell-mediated cytotoxicity using effector cell suspensions derived from peripheral blood mononuclear cells (PBMCs) isolated from the peripheral blood of two normal subjects. The horizontal axis represents antibody concentration (μg/mL) and the vertical axis represents cell-mediated cytotoxicity (%).

FIG. 8 presents graphs showing the neutralizing activity of ADCC-active 6D6 chimeric antibodies against pseudotype ebolaviruses.

DESCRIPTION OF EMBODIMENTS

Figure 4:
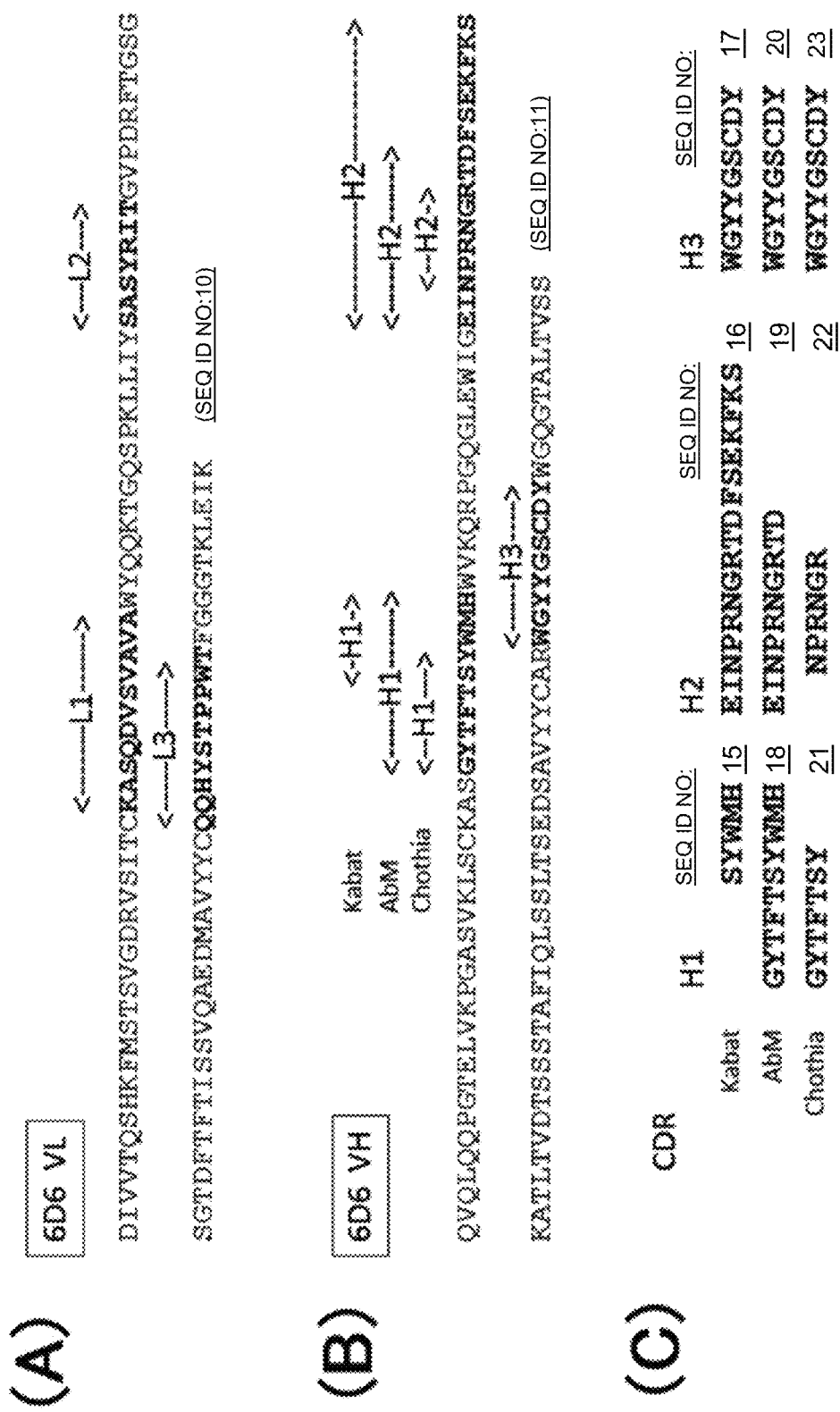
FIG. 4 shows the variable regions of mouse monoclonal antibody 6D6. (A) Light chain variable region along with CDR regions 1 to 3. (B) Heavy chain variable region along with CDR regions 1 to 3. (C) CDR regions 1 to 3 in the heavy chain variable region.

The present invention will be described in more detail below. The following embodiments are illustrated to describe the present invention, and it is not intended to limit the present invention only to these embodiments. The present invention can be implemented in various modes, without departing from the spirit of the invention.

It should be noted that all publications, patent application publications, patent gazettes and other patent documents cited herein, are incorporated herein by reference. Moreover, this specification incorporates the contents disclosed in the specification and drawings of Japanese Patent Application No. 2015-161567 (filed on Aug. 19, 2015), based on which the present application claims priority.

1. Monoclonal Antibody of the Present Invention

The present invention is directed to a monoclonal antibody or an antigen-binding fragment thereof which recognizes an internal fusion loop (IFL) of surface glycoprotein GP of ebolavirus and is capable of neutralizing the biological activity of ebolavirus (hereinafter referred to as "the monoclonal antibody of the present invention"). Typically, the monoclonal antibody of the present invention binds to an epitope present in an internal fusion loop of surface GP of ebolavirus.

The expression "recognize an internal fusion loop" is intended to mean binding (preferably specifically binding) to an epitope present in an internal fusion loop of ebolavirus GP. The phrase "specifically binding" actually means a state where a specific antigen-antibody reaction is detectable by immunoassays such as enzyme immunoassay, etc.

The expression "capable of neutralizing the biological activity of ebolavirus" is intended to mean that the monoclonal antibody of the present invention binds to an internal fusion loop of ebolavirus GP to thereby inhibit the biological activity of ebolavirus. Such activity is hereinafter also referred to as "neutralizing activity." The expression "inhibit the biological activity" is intended to mean causing a reduction of about 5% to 100%, preferably 10% to 100%, more preferably 20% to 100%, more preferably 30% to 100%, more preferably 40% to 100%, more preferably 50% to 100%, more preferably 60% to 100%, more preferably 70% to 100%, even more preferably 80% to 100% in the biological activity of ebolavirus resulting from its antigen (i.e., an internal fusion loop of ebolavirus GP).

Alternatively, the expression "capable of neutralizing the biological activity of ebolavirus" is intended to mean that the antibody of the present invention has a 50% inhibitory concentration ($IC_{50}$) of 0.01 to 0.10 µg/ml, 0.03 to 0.90 µg/ml, 0.05 to 0.80 µg/ml, 0.10 to 0.70 µg/ml, 0.10 to 0.69 µg/ml, 0.10 to 0.68 µg/ml, 0.10 to 0.67 µg/ml, 0.10 to 0.66 µg/ml, 0.10 to 0.65 µg/ml, 0.10 to 0.64 µg/ml, 0.10 to 0.63 µg/ml, or 0.10 to 0.62 µg/ml against ebolavirus. Most preferably, the neutralizing activity $IC_{50}$ is 0.12 to 0.62 µg/ml.

The biological activity intended here may be exemplified by virus infectivity. Virus infectivity may be measured as described below in the Examples.

The term "antibody" refers to an immunoglobulin molecule composed of four polypeptide chains, i.e., two heavy chains (H chains) and two light chains (L chains) which are linked to each other via disulfide bonds. Each H chain is composed of an H chain variable region (also referred to as "HCVR" or "$V_H$") and an H chain constant region (which consists of three domains, also referred to as "$C_H1$," "$C_H2$" and "$C_H3$," respectively (collectively referred to as $C_H$)). Each L chain is composed of an L chain variable region (also referred to as "LCVR" or "$V_L$") and an L chain constant region (which consists of one domain, also referred to as "$C_L$").

In particular, HCVR and LCVR are important in terms of being involved in the binding specificity of antibody. Since an antibody interacts with its target antigen via amino acid residues in LCVR and HCVR, amino acid sequences within these variable regions vary more greatly among individual antibodies than sequences located outside the variable regions. Moreover, HCVR and LCVR can also be subdivided into regions referred to as framework regions (FRs), which are kept more constant among various antibodies, and hypervariable regions referred to as complementarity determining regions (CDRs). HCVR and LCVR are each composed of three CDRs and four FRs, which are arranged in the order of FR1, CDR1, FR2, CDR2, FR3, CDR3 and FR4 from the amino-terminal end to the carboxy-terminal end.

There are several reports about the definition of CDRs and the method of determination of their positions, and these may all be used. For example, the definition of Kabat (Sequences of proteins of immunological interest, 5th ed., U.S. Department of Health and Human Services, 1991) or the definition of Chothia (Chothia et al., J. Mol. Biol., 1987; 196:901-917) may be used. Alternatively, in some cases, the definition of Kabat and the definition of Chothia may both be taken into consideration for CDR determination. For example, a region overlapping between CDRs according to the respective definitions or a region containing both CDRs according to the respective definitions may be defined as CDR. By way of actual example, it is possible to use the definition of AbM (i.e., the method of Martin et al. using the AbM antibody modeling software of Oxford Molecular Ltd. (Proc. Natl. Acad. Sci. USA, 1989; 86:9268-9272)), which is an eclectic approach between the definition of Kabat and the definition of Chothia.

The term "monoclonal antibody" refers to an antibody molecule derived from single antibody-producing cells. The term "monoclonal antibody" used herein is not limited to antibodies produced by hybridoma technology. The term "monoclonal antibody" includes any clones of eukaryotic organisms, prokaryotic organisms or phages, but its method of production is not limited.

The term "antigen-binding fragment" refers to a portion of the full-length antibody, which has the binding ability to an antigen, as in the case of the full-length antibody, and is generally intended to mean a portion containing an antigen-binding region or a variable region. In the monoclonal antibody of the present invention, examples of an antigen-binding fragment include Fab, Fab', F(ab')$_2$, Fv (variable fragment of antibody), single chain antibody (e.g., H chain, L chain, H chain V region, and L chain V region), scFv, diabody (scFv dimer), dsFv (disulfide stabilized V region), and a peptide containing a complementarity determining region (CDR) as at least a part thereof, etc.

It should be noted that the term "monoclonal antibody or an antigen-binding fragment thereof" is herein also referred to as the "monoclonal antibody" for simplification purposes.

The term "epitope" refers to an antigen site which is recognized by an antibody or an antigen-binding fragment thereof. Such an epitope comprises one or more (e.g., 10 or more, 9 or more, 8 or more, 7 or more, 6 or more, 5 or more, 4 or more, 3 or more, 2 or more, or 1 or more) amino acid residues and may be formed from either contiguous amino acids or non-contiguous amino acids juxtaposed upon three-dimensional protein folding, by way of example. As an epitope to be recognized by the antibody of the present invention, preferred is an epitope present in an internal fusion loop of ebolavirus GP, as specifically exemplified by an epitope containing Gly located at position 18 of the GP internal fusion loop.

The monoclonal antibody of the present invention may be a chimeric antibody, a humanized antibody or a human antibody. This is because the monoclonal antibody of the present invention retains the same level of neutralizing activity even in the form of a chimeric antibody, a humanized antibody or a human antibody. Moreover, the monoclonal antibody of the present invention includes a mouse antibody, a rat antibody, a human-type chimeric antibody, a humanized antibody and a human antibody, each being prepared by gene recombination technology.

The term "chimeric antibody" is intended to mean an antibody in which the sequences of H chain and L chain variable regions ($V_H$ and $V_L$) are derived from one mammalian species, while the sequences of constant regions ($C_M$ and $C_L$) are derived from another mammalian species. The sequences of the variable regions are preferably derived from an animal species (e.g., mouse) from which hybridomas can be easily prepared, whereas the sequences of the constant regions are preferably derived from a mammalian species intended as a target of administration. Chimeric antibody is, for example, a mouse-human chimeric antibody.

The term "humanized antibody" is intended to mean an antibody in which the sequences of all regions but complementarity determining regions (CDRs) present in the variable regions (i.e., constant regions and FRs in the variable regions) are of human origin, while only the CDR sequences are derived from another mammalian species. As another mammalian species, preferred is an animal species (e.g., mouse) from which hybridomas can be easily prepared, by way of example.

The term "human antibody" is intended to mean an antibody in which all the sequences of both light and heavy chains including CDRs are essentially derived from human genes.

In a preferred embodiment, the monoclonal antibody of the present invention is a monoclonal antibody against one or more species (i.e., one species, two species, three species, four species or five species) among the five ebolavirus species, i.e., Zaire ebolavirus, Sudan ebolavirus, Tai Forest ebolavirus, Bundibugyo ebolavirus and Reston ebolavirus. In a particularly preferred embodiment, the monoclonal antibody of the present invention is a cross-reactive monoclonal antibody against all the five ebolavirus species.

GP in which the internal fusion loop to be recognized by the monoclonal antibody of the present invention is present is the glycoprotein of ebolavirus. Ebolavirus is a negative-strand RNA virus and forms a filamentous virus particle. This virus particle is covered with an envelope, which is a lipid bilayer derived from host cells, and comprises seven structural proteins including GP. GP, which is one of the structural proteins, is a glycoprotein present in the envelope and is responsible for adsorption onto and invasion into host cells.

Structural proteins other than GP are NP, VP35, VP40, VP30, VP24 and L. VP40 is a matrix protein and is present inside the envelope to support the envelope. VP24 has affinity for the membrane and is considered to be a minor matrix protein. NP, VP30 and VP35 are nucleoproteins, while L is a polymerase protein. These nucleoproteins and polymerase protein bind to genomic RNA to thereby form a helical nucleocapsid.

GP particularly varies in its amino acid sequence among the five ebolavirus species. Information about the GP amino acid sequences of Zaire ebolavirus, Sudan ebolavirus, Bundibugyo ebolavirus, Tai Forest ebolavirus and Reston ebolavirus can be obtained when referring to, for example, the sequences under Accession No. U2 23187.1, Accession No. U23069.1, Accession No. NC_014373.1, Accession No. U28006.1 and Accession No. U23152.1, respectively, in a publicly accessible sequence database such as GenBank.

The internal fusion loop present in ebolavirus GP also varies in its amino acid sequence among the five ebolavirus species. The internal fusion loop is present at positions 511 to 556 of the GP amino acid sequence in Zaire ebolavirus, Sudan ebolavirus, Bundibugyo ebolavirus, Tai Forest ebolavirus and Reston ebolavirus, while it is present at positions 512 to 557 in Reston ebolavirus. In more detail, the amino acid sequences of GP internal fusion loops of Zaire ebolavirus, Sudan ebolavirus, Bundibugyo ebolavirus, Tai Forest ebolavirus and Reston ebolavirus are as of SEQ ID NO: 1, SEQ ID NO: 2, SEQ ID NO: 3, SEQ ID NO: 4 and SEQ ID NO: 5, respectively.

In a preferred embodiment, the monoclonal antibody of the present invention recognizes an internal fusion loop of ebolavirus GP of one or more species (i.e., one species, two species, three species, four species or five species). In more detail, the monoclonal antibody of the present invention recognizes at least one (i.e., one, two, three, four or five) GP internal fusion loop selected from the group consisting of an internal fusion loop consisting of the amino acid sequence of SEQ ID NO: 1, a GP internal fusion loop consisting of the amino acid sequence of SEQ ID NO: 2, a GP internal fusion loop consisting of the amino acid sequence of SEQ ID NO: 3, a GP internal fusion loop consisting of the amino acid sequence of SEQ ID NO: 4, and a GP internal fusion loop consisting of the amino acid sequence of SEQ ID NO: 5. In a particularly preferred embodiment, the monoclonal antibody of the present invention recognizes all of an internal fusion loop consisting of the amino acid sequence of SEQ ID NO: 1, a GP internal fusion loop consisting of the amino acid sequence of SEQ ID NO: 2, a GP internal fusion loop consisting of the amino acid sequence of SEQ ID NO: 3, a GP internal fusion loop consisting of the amino acid sequence of SEQ ID NO: 4, and a GP internal fusion loop consisting of the amino acid sequence of SEQ ID NO: 5.

Moreover, the monoclonal antibody of the present invention does not recognize at least one GP internal fusion loop selected from an internal fusion loop consisting of amino acids comprising Lys or Glu substituted for Gly at position 18 in the amino acid sequence of SEQ ID NO: 1, an internal fusion loop consisting of amino acids comprising His substituted for Tyr at position 6, Ala substituted for Val at position 11 and Trp substituted for Leu at position 19 in SEQ ID NO: 5, and an internal fusion loop consisting of amino acids comprising Glu substituted for Gly at position 18 in SEQ ID NO: 5.

In a certain embodiment, the monoclonal antibody of the present invention may have antibody-dependent cell-mediated cytotoxicity. Such an antibody may also be referred to as "ADCC-active antibody." The term "antibody-dependent cell-mediated cytotoxicity (ADCC)" refers to cell-mediated cytotoxicity induced in an antibody-dependent manner when the Fc region of an antibody bound to its antigen binds to the Fc receptor on effector cells such as natural killer cells, macrophages, neutrophils, eosinophils and mononuclear cells (e.g., peripheral blood mononuclear cells). Thus, in this embodiment, the monoclonal antibody of the present invention binds to ebolavirus (any of Zaire ebolavirus, Sudan ebolavirus, Bundibugyo ebolavirus, Tai Forest ebolavirus and Reston ebolavirus) serving as an antigen, and the Fc region of this antibody binds to the Fc receptor on effector cells such as natural killer cells, macrophages, neutrophils, eosinophils and other cells to thereby induce cell-mediated cytotoxicity in an antibody-dependent manner.

In a preferred embodiment, the present invention provides a monoclonal antibody or an antigen-binding fragment thereof, which recognizes an internal fusion loop of ebolavirus GP and is capable of neutralizing the biological activity of ebolavirus, whose light chain variable region comprises CDR1 to CDR3 in a light chain variable region consisting of the amino acid sequence of SEQ ID NO: 10 or mutated CDR1 to CDR3 thereof, and whose heavy chain variable region comprises CDR1 to CDR3 in a heavy chain variable region consisting of the amino acid sequence of SEQ ID NO: 11 or mutated CDR1 to CDR3 thereof.

The amino acid sequence of a monoclonal antibody variable region is responsible for the major pan of antibody-antigen interaction; and hence when an expression vector is constructed to comprise a variable region sequence or CDR region sequences thereof derived from a certain naturally occurring antibody in a state being grafted to a constant region or framework sequence derived from a different antibody having different properties, the thus constructed expression vector allows expression of a recombinant antibody mimicking the properties of the certain naturally occurring antibody.

In this case, to reconstruct an intact recombinant antibody having the same binding properties as the original antibody, there is no necessity to obtain the entire sequence of the certain antibody. Only the heavy and light chain variable region sequences of the antibody or their CDR region sequences may be sufficient for this purpose.

CDR1 to CDR3 in a light chain variable region consisting of the amino acid sequence of SEQ ID NO: 10 consist of the amino acid sequences of SEQ ID NO: 12, SEQ ID NO: 13 and SEQ ID NO: 14, respectively.

CDR1 to CDR3 in a heavy chain variable region consisting of the amino acid sequence of SEQ ID NO: 11 consist of the amino acid sequences of SEQ ID NO: 15, SEQ ID NO: 16 and SEQ ID NO: 17, respectively, according to the definition of Kabat.

CDR1 to CDR3 in a heavy chain variable region consisting of the amino acid sequence of SEQ ID NO: 11 consist of the amino acid sequences of SEQ ID NO: 18, SEQ ID NO: 19 and SEQ ID NO: 20, respectively, according to the definition of AbM.

CDR1 to CDR3 in a heavy chain variable region consisting of the amino acid sequence of SEQ ID NO: 11 consist of the amino acid sequences of SEQ ID NO: 21, SEQ ID NO: 22 and SEQ ID NO: 23, respectively, according to the definition of Chothia.

The present invention is preferably directed to a monoclonal antibody or an antigen-binding fragment thereof, which recognizes an internal fusion loop of ebolavirus GP and is capable of neutralizing the biological activity of ebolavirus, wherein the monoclonal antibody or antigen-binding fragment thereof is any of the following:

(a) a monoclonal antibody or an antigen-binding fragment thereof, which comprises:

a light chain variable region comprising:

light chain CDR1 consisting of an amino acid sequence selected from the group consisting of the amino acid sequence of SEQ ID NO: 12; an amino acid sequence mutated to have deletion, substitution, insertion and/or addition of one to several amino acid residues in the amino acid sequence of SEQ ID NO: 12; and an amino acid sequence having an identity of 90% or more with the amino acid sequence of SEQ ID NO: 12, light chain CDR2 consisting of an amino acid sequence selected from the group consisting of the amino acid sequence of SEQ ID NO: 13; an amino acid sequence mutated to have deletion, substitution, insertion and/or addition of one to several amino acid residues in the amino acid sequence of SEQ ID NO: 13; and an amino acid sequence having an identity of 90% or more with the amino acid sequence of SEQ ID NO: 13, and light chain CDR3 consisting of an amino acid sequence selected from the group consisting of the amino acid sequence of SEQ ID NO: 14; an amino acid sequence mutated to have deletion, substitution, insertion and/or addition of one to several amino acid residues in the amino acid sequence of SEQ ID NO: 14; and an amino acid sequence having an identity of 90% or more with the amino acid sequence of SEQ ID NO: 14; and a heavy chain variable region comprising:

heavy chain CDR1 consisting of an amino acid sequence selected from the group consisting of the amino acid sequence of SEQ ID NO: 15; an amino acid sequence mutated to have deletion, substitution, insertion and/or addition of one to several amino acid residues in the amino acid sequence of SEQ ID NO: 15; and an amino acid sequence having an identity of 90% or more with the amino acid sequence of SEQ ID NO: 15, heavy chain CDR2 consisting of an amino acid sequence selected from the group consisting of the amino acid sequence of SEQ ID NO: 16; an amino acid sequence mutated to have deletion, substitution, insertion and/or addition of one to several amino acid residues in the amino acid sequence of SEQ ID NO: 16; and an amino acid sequence having an identity of 90% or more with the amino acid sequence of SEQ ID NO: 16, and heavy chain CDR3 consisting of an amino acid sequence selected from the group consisting of the amino acid sequence of SEQ ID NO: 17; an amino acid sequence mutated to have deletion, substitution, insertion and/or addition of one to several amino acid residues in the amino acid sequence of SEQ ID NO: 17; and an amino acid sequence having an identity of 90% or more with the amino acid sequence of SEQ ID NO: 17;

(b) a monoclonal antibody or an antigen-binding fragment thereof, which comprises:

a light chain variable region comprising:

light chain CDR1 consisting of an amino acid sequence selected from the group consisting of the amino acid sequence of SEQ ID NO: 12; an amino acid sequence mutated to have deletion, substitution, insertion and/or addition of one to several amino acid residues in the amino acid sequence of SEQ ID NO: 12; and an amino acid sequence having an identity of 90% or more with the amino acid sequence of SEQ ID NO: 12, light chain CDR2 consisting of an amino acid sequence selected from the group consisting of the amino acid sequence of SEQ ID NO: 13; an amino acid sequence mutated to have deletion, substitution, insertion and/or addition of one to several amino acid residues in the amino acid sequence of SEQ ID NO: 13; and an amino acid sequence having an identity of 90% or more with the amino acid sequence of SEQ ID NO: 13, and light chain CDR3 consisting of an amino acid sequence selected from the group consisting of the amino acid sequence of SEQ ID NO: 14; an amino acid sequence mutated to have deletion, substitution, insertion and/or addition of one to several amino acid residues in the amino acid sequence of SEQ ID NO: 14; and an amino acid sequence having an identity of 90% or more with the amino acid sequence of SEQ ID NO: 14; and a heavy chain variable region comprising:

heavy chain CDR1 consisting of an amino acid sequence selected from the group consisting of the amino acid sequence of SEQ ID NO: 18; an amino acid sequence mutated to have deletion, substitution, insertion and/or addition of one to several amino acid residues in the amino acid sequence of SEQ ID NO: 18; and an amino acid sequence having an identity of 90% or more with the amino acid sequence of SEQ ID NO: 18, heavy chain CDR2 consisting of an amino acid sequence selected from the group consisting of the amino acid sequence of SEQ ID NO: 19; an amino acid sequence mutated to have deletion, substitution, insertion and/or addition of one to several amino acid residues in the amino acid sequence of SEQ ID NO: 19; and an amino acid sequence having an identity of 90% or more with the amino acid sequence of SEQ ID NO: 19, and heavy chain CDR3 consisting of an amino acid sequence selected from the group consisting of the amino acid sequence of SEQ ID NO: 20; an amino acid sequence mutated to have deletion, substitution, insertion and/or addition of one to several amino acid residues in the amino acid sequence of SEQ ID NO: 20; and an amino acid sequence having an identity of 90% or more with the amino acid sequence of SEQ ID NO: 20; as well as (c) a monoclonal antibody or an antigen-binding fragment thereof, which comprises:

a light chain variable region comprising:

light chain CDR1 consisting of an amino acid sequence selected from the group consisting of the amino acid sequence of SEQ ID NO: 12; an amino acid sequence mutated to have deletion, substitution, insertion and/or addition of one to several amino acid residues in the amino acid sequence of SEQ ID NO: 12; and an amino acid sequence having an identity of 90% or more with the amino acid sequence of SEQ ID NO: 12, light chain CDR2 consisting of an amino acid sequence selected from the group consisting of the amino acid sequence of SEQ ID NO: 13; an amino acid sequence mutated to have deletion, substitution, insertion and/or addition of one to several amino acid residues in the amino acid sequence of SEQ ID NO: 13; and an amino acid sequence having an identity of 90% or more with the amino acid sequence of SEQ ID NO: 13, and light chain CDR3 consisting of an amino acid sequence selected from the group consisting of the amino acid sequence of SEQ ID NO: 14; an amino acid sequence mutated to have deletion, substitution, insertion and/or addition of one to several amino acid residues in the amino acid sequence of SEQ ID NO: 14; and an amino acid sequence having an identity of 90% or more with the amino acid sequence of SEQ ID NO: 14; and a heavy chain variable region comprising:

heavy chain CDR1 consisting of an amino acid sequence selected from the group consisting of the amino acid sequence of SEQ ID NO: 21; an amino acid sequence mutated to have deletion, substitution, insertion and/or addition of one to several amino acid residues in the amino acid sequence of SEQ ID NO: 21; and an amino acid sequence having an identity of 90% or more with the amino acid sequence of SEQ ID NO: 21, heavy chain CDR2 consisting of an amino acid sequence selected from the group consisting of the amino acid sequence of SEQ ID NO: 22; an amino acid sequence mutated to have deletion, substitution, insertion and/or addition of one to several amino acid residues in the amino acid sequence of SEQ ID NO: 22; and an amino acid sequence having an identity of 90% or more with the amino acid sequence of SEQ ID NO: 22, and heavy chain CDR3 consisting of an amino acid sequence selected from the group consisting of the amino acid sequence of SEQ ID NO: 23; an amino acid sequence mutated to have deletion, substitution, insertion and/or addition of one to several amino acid residues in the amino acid sequence of SEQ ID NO: 23; and an amino acid sequence having an identity of 90% or more with the amino acid sequence of SEQ ID NO: 23.

In some embodiments of the present invention, there is no particular limitation on the amino acid sequences, except for CDRs, in the light chain and/or heavy chain variable region, and so-called CDR-grafted antibodies whose amino acid sequences, except for CDRs, are derived from other antibodies, particularly antibodies of other species, are also included in the antibody of the present invention. Among them, preferred is a humanized antibody whose amino acid sequences, except for CDRs, are also of human origin, but a humanized antibody may optionally be mutated to have deletion, substitution, insertion and/or addition of one to several amino acid residues in its framework regions (FRs).

As used herein, the expression "mutated to have deletion, substitution, insertion and/or addition of one to several amino acid residues" is intended to mean that deletion, substitution, insertion and/or addition of one or several amino acid residues occurs at any one or several amino acid positions in the same sequence, and, two or more of deletion, substitution, insertion and addition may occur at the same time. The phrase "one to several" in the expression "deletion, substitution, insertion and/or addition of one to several amino acid residues" is intended to mean, for example, 5 amino acid residues, 4 amino acid residues, 3 amino acid residues, 2 amino acid residues or a single amino acid residue. In general, a smaller number is more preferred for the above deletion, substitution, insertion and/or addition of amino acid residues.

Examples of mutually interchangeable amino acid residues are shown below. Amino acid residues included in the same group are interchangeable with each other.

Group A: leucine, isoleucine, norleucine, valine, norvaline, alanine, 2-aminobutanoic acid, methionine, o-methylserine, t-butylglycine, t-butylalanine, cyclohexylalanine;

Group B: aspartic acid, glutamic acid, isoaspartic acid, isoglutamic acid, 2-aminoadipic acid, 2-aminosuberic acid;

Group C: asparagine, glutamine;

Group D: lysine, arginine, ornithine, 2,4-diaminobutanoic acid, 2,3-diaminopropionic acid;

Group E: proline, 3-hydroxyproline, 4-hydroxyproline;

Group F: serine, threonine, homoserine;

Group G: phenylalanine, tyrosine.

As used herein, the range of "900/s or more" in the expression "amino acid sequence having an identity of 90% or more" is, for example, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. In general, a larger value is more preferred for the above identity. The identity of amino acid sequences or nucleotide sequences can be determined by using the analysis program of BLAST (see, e.g., Altzshul S. F. et al., J. Mol. Biol. 215, 403(1990)). If BLAST is used, default parameters in each program may be used.

In a preferred embodiment, the present invention provides a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and a heavy chain variable region comprising heavy chain CDR1 consisting of the amino acid sequence of SEQ ID NO: 15, heavy chain CDR2 consisting of the amino acid sequence of SEQ ID NO: 16, and heavy chain CDR3 consisting of the amino acid sequence of SEQ ID NO: 17 in which Cys at position 7 is replaced with another amino acid residue. Cys residues contained in the CDR sequences are preferably replaced with other amino acid residues in terms of antibody homogeneity and stability, and may be replaced with any amino acid residues as long as the replacement of Cys residues with other amino acid residues results in an antibody whose binding activity is equal to that of the original antibody before amino acid residue replacement. Preferred examples of other amino acid residues include amino acid residues such as Ser, Ala, etc.

In a more preferred embodiment, the present invention provides a monoclonal antibody or an antigen-binding fragment thereof, which recognizes an internal fusion loop of ebolavirus GP and is capable of neutralizing the biological activity of ebolavirus, wherein the monoclonal antibody or antigen-binding fragment thereof is any one selected from: a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and a heavy chain variable region comprising heavy chain CDR1 consisting of the amino acid sequence of SEQ ID NO: 15, heavy chain CDR2 consisting of the amino acid sequence of SEQ ID NO: 16, and heavy chain CDR3 consisting of the amino acid sequence of SEQ ID NO: 17; a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and a heavy chain variable region comprising heavy chain CDR1 consisting of the amino acid sequence of SEQ ID NO: 15, heavy chain CDR2 consisting of the amino acid sequence of SEQ ID NO: 16, and heavy chain CDR3 consisting of the amino acid sequence of SEQ ID NO: 40; and a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and a heavy chain variable region comprising heavy chain CDR1 consisting of the amino acid sequence of SEQ ID NO: 15, heavy chain CDR2 consisting of the amino acid sequence of SEQ ID NO: 16, and heavy chain CDR3 consisting of the amino acid sequence of SEQ ID NO: 41.

In another more preferred embodiment, the present invention provides a monoclonal antibody or an antigen-binding fragment thereof, which recognizes an internal fusion loop of ebolavirus GP and is capable of neutralizing the biological activity of ebolavirus, wherein the monoclonal antibody or antigen-binding fragment thereof is any one selected from: a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and a heavy chain variable region comprising heavy chain CDR1 consisting of the amino acid sequence of SEQ ID NO: 18, heavy chain CDR2 consisting of the amino acid sequence of SEQ ID NO: 19, and heavy chain CDR3 consisting of the amino acid sequence of SEQ ID NO: 20; a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and a heavy chain variable region comprising heavy chain CDR1 consisting of the amino acid sequence of SEQ ID NO: 18, heavy chain CDR2 consisting of the amino acid sequence of SEQ ID NO: 19, and heavy chain CDR3 consisting of the amino acid sequence of SEQ ID NO: 40; and a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and a heavy chain variable region comprising heavy chain CDR1 consisting of the amino acid sequence of SEQ ID NO: 18, heavy chain CDR2 consisting of the amino acid sequence of SEQ ID NO: 19, and heavy chain CDR3 consisting of the amino acid sequence of SEQ ID NO: 41.

In yet another more preferred embodiment, the present invention provides a monoclonal antibody or an antigen-binding fragment thereof, which recognizes an internal fusion loop of ebolavirus GP and is capable of neutralizing the biological activity of ebolavirus, wherein the monoclonal antibody or antigen-binding fragment thereof is any one selected from: a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ 1D NO: 14, and a heavy chain variable region comprising heavy chain CDR1 consisting of the amino acid sequence of SEQ ID NO: 21, heavy chain CDR2 consisting of the amino acid sequence of SEQ ID NO: 22, and heavy chain CDR3 consisting of the amino acid sequence of SEQ ID NO: 23; a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and a heavy chain variable region comprising heavy chain CDR1 consisting of the amino acid sequence of SEQ ID NO: 21, heavy chain CDR2 consisting of the amino acid sequence of SEQ ID NO: 22, and heavy chain CDR3 consisting of the amino acid sequence of SEQ ID NO: 40; and a monoclonal antibody which comprises a light chain variable region comprising light chain CDR1 consisting of the amino acid sequence of SEQ ID NO: 12, light chain CDR2 consisting of the amino acid sequence of SEQ ID NO: 13, and light chain CDR3 consisting of the amino acid sequence of SEQ ID NO: 14, and a heavy chain variable region comprising heavy chain CDR1 consisting of the amino acid sequence of SEQ ID NO: 21, heavy chain CDR2 consisting of the amino acid sequence of SEQ ID NO: 22, and heavy chain CDR3 consisting of the amino acid sequence of SEQ ID NO: 41.

In some embodiments, the present invention provides a monoclonal antibody or an antigen-binding fragment thereof, which recognizes an internal fusion loop of ebolavirus GP and is capable of neutralizing the biological activity of ebolavirus, wherein the monoclonal antibody or antigen-binding fragment thereof comprises:

a light chain variable region consisting of an amino acid sequence selected from the group consisting of the amino acid sequence of SEQ ID NO: 10; an amino acid sequence mutated to have deletion, substitution, insertion and/or addition of one to several amino acid residues in the amino acid sequence of SEQ ID NO: 10; and an amino acid sequence having an identity of 90% or more with the amino acid sequence of SEQ ID NO: 10; and a heavy chain variable region consisting of an amino acid sequence selected from the group consisting of the amino acid sequence of SEQ ID NO: 11; an amino acid sequence mutated to have deletion, substitution, insertion and/or addition of one to several amino acid residues in the amino acid sequence of SEQ ID NO: 11; and an amino acid sequence having an identity of 90% or more with the amino acid sequence of SEQ ID NO: 11.

In a preferred embodiment, the present invention provides a monoclonal antibody or an antigen-binding fragment thereof, which recognizes an internal fusion loop of ebolavirus GP and is capable of neutralizing the biological activity of ebolavirus, wherein the monoclonal antibody or antigen-binding fragment thereof comprises:

a light chain variable region consisting of the amino acid sequence of SEQ ID NO: 10; and a heavy chain variable region consisting of the amino acid sequence of SEQ ID NO: 11.

In some embodiments, the present invention provides a monoclonal antibody or an antigen-binding fragment thereof, which recognizes an internal fusion loop of ebolavirus GP and is capable of neutralizing the biological activity of ebolavirus, wherein the monoclonal antibody or antigen-binding fragment thereof comprises a light chain consisting of the amino acid sequence of SEQ ID NO: 24 and a heavy chain consisting of the amino acid sequence of SEQ ID NO: 25.

The genetically recombinant antibody of the present invention may be prepared in any manner as long as it is an antibody prepared by gene recombination technology, and a gene encoding a desired genetically recombinant antibody is inserted into an expression vector and then transfected into appropriate host cells. Then, these antibody gene-expressing cells (or transformed cells) are cultured and the antibody is purified from the culture supernatant, whereby the genetically recombinant antibody can be prepared.

For preparation of a mouse antibody, a rat antibody or a chimeric antibody, known gene recombination technology may be used for its construction.

For preparation of a humanized antibody, reconstituted variable regions whose framework regions (FRs) are of human origin and whose CDRs are of mouse origin are prepared by grafting complementarity determining regions (CDRs) from mouse antibody variable regions to human variable regions (so-called CDR grafting). Then, these humanized reconstituted human variable regions are linked to human constant regions. General procedures for preparation of such a humanized antibody are well known in the art (see, e.g., Nature, 321, 522-525(1986); J. Mol. Biol., 196, 901-917(1987); Queen C et al., Proc. Natl. Acad. Sci. USA, 86:10029-10033(1989); JP H04-502408 A).

The amino acid sequences of human antibody frameworks, which can be used as framework materials in the preparation of a humanized antibody include the amino acid sequences of SEQ ID NO: 36 and SEQ ID NO: 37 for light chain frameworks, and the amino acid sequences of SEQ ID NO: 38 and SEQ ID NO: 39 for heavy chain frameworks.

Techniques for preparation of a human antibody are also known, and in the case of gene sequences common to humans, an approach has been established for their preparation by genetic engineering procedures. A human antibody may be obtained, for example, by using human antibody-producing mice which have human chromosome fragments comprising genes for human antibody H chain and L chain (see, e.g., Tomizuka, K. et al., Nature Genetics, (1977) 16, 133-143; Kuroiwa, Y. et. al., Nuc. Acids Res., (1998) 26, 3447-3448; Yoshida, 1-1. et. al., Animal Cell Technology: Basic and Applied Aspects. (1999) 10, 69-73 (Kitagawa, Y., Matuda, T. and Iijima, S. eds.). Kluwer Academic Publishers; Tomizuka, K. et. al., Proc. Natl. Acad. Sci. USA, (2000) 97, 722-727) or by obtaining a phage display-derived human antibody selected from human antibody libraries (see, e.g., Wormstone, I. M. et. al, Investigative Ophthalmology & Visual Science., (2002) 43(7), 2301-8; Carmen, S. et. al., Briefings in Functional Genomics and Proteomics, (2002) 1(2), 189-203; Siriwardena, D. et. al., Opthalmology, (2002) 109(3), 427-431).

2. Isolated Nucleic Acid Molecule of the Present Invention

The present invention provides an isolated nucleic acid molecule encoding the monoclonal antibody of the present invention (hereinafter also referred to as "the isolated nucleic acid molecule of the present invention"). The term "nucleic acid molecule" refers to RNA or DNA, preferably DNA. DNA includes genomic DNA, a genomic DNA library, cDNA, a cDNA library, synthetic DNA and so on. Vectors for use in these libraries are not limited in any way and may be any of bacteriophages, plasmids, cosmids, phagemids and so on.

DNA encoding the monoclonal antibody of the present invention is easily separated and sequenced in a standard manner (e.g., by using oligonucleotide probes capable of specifically binding to genes encoding the heavy and light chains of the monoclonal antibody of the present invention). Hybridoma cells producing the monoclonal antibody serve as a preferred source of such DNA.

3. Expression Vector of the Present Invention, and Transformed Cell of the Present Invention The present invention provides a vector constructed to carry the isolated nucleic acid molecule of the present invention (hereinafter referred to as "the expression vector of the present invention"), and a transformed cell transfected with this expression vector (hereinafter referred to as "the transformed cell of the present invention").

(1) Expression Vector of the Present Invention

The isolated nucleic acid molecule of the present invention is inserted into an expression vector in an attempt to synthesize the monoclonal antibody in a recombinant host cell. In some embodiments, two nucleic acid molecules may each be used as the isolated nucleic acid molecule of the present invention, and they may be inserted into separate expression vectors, respectively (e.g., the heavy chain may be inserted into the first expression vector, and the light chain may be inserted into the second expression vector), or alternatively, they may be inserted into the same expression vector.

The expression vector is not limited in any way as long as it is replicable in the host, and examples include plasmids, bacteriophages, animal viruses, etc.

The isolated nucleic acid molecule of the present invention is generally ligated in an expressible manner downstream of a promoter in an appropriate vector.

In addition to the above elements, the expression vector of the present invention may further comprise an enhancer, a splicing signal, a polyA addition signal, a ribosome binding sequence (SD sequence), a selection marker and so on, if desired. Examples of a selection marker include the dihydrofolate reductase gene, the ampicillin resistance gene, the neomycin resistance gene, etc.

(2) Transformed Cell of the Present Invention

The thus obtained expression vector of the present invention may be introduced into an appropriate host cell to thereby prepare a transformed cell. Any host cell may be used for this purpose as long as it is capable of expressing the isolated nucleic acid molecule of the present invention, and examples include bacteria (e.g., E. coli), actinomycetes, yeast, insect cells (e.g., SF9), mammalian cells (e.g., human HEK293 embryonic kidney-derived cells, monkey COS cells, Chinese hamster ovary (CHO) cells, myeloma cells), etc. CHO cells available for use include CHO-K1 (ATCC CCL-61), DUKXB11 (ATCC CCL-9096), Pro-5 (ATCC CCL-1781), CHO-S (Life Technologies, Cat #11619), CHO cells deficient in the dihydrofolate reductase gene (hereinafter abbreviated as dhfr) [Proc. Natl. Acad. Sci. USA, 77, 4216 (1980)] and CHO cells deficient in the α1,6-fucosyltransferase gene (WO02005/035586), etc.

Introduction of the expression vector into a host cell and transformation thereby may be accomplished by commonly used various techniques. Techniques for introduction of an expression vector into a host cell include calcium phosphate transfection (Virology, 52, 456-457 (1973)), lipofection (Proc. Natl. Acad. Sci. USA, 84, 7413 (1987)), electroporation (EMBO J., 1, 841-845 (1982)) and so on. In this way, a transformant transformed with the expression vector of the present invention can be obtained.

4. How to Prepare the Monoclonal Antibody of the Present Invention

An explanation will be given of how to prepare the monoclonal antibody of the present invention.

Without being limited thereto, the monoclonal antibody of the present invention may be prepared, for example, as follows: the transformed cell of the present invention may be cultured under conditions suitable for expression of the monoclonal antibody of the present invention and the cultured product (e.g., culture supernatant) may be treated to purify the monoclonal antibody of the present invention produced in the transformed cell. In some embodiments, the monoclonal antibody of the present invention may be prepared such that its heavy chain is produced in one cell and its light chain is produced in another cell.

The monoclonal antibody of the present invention may also be produced in transgenic animals such as cows and chickens.

Alternatively, the monoclonal antibody of the present invention may also be prepared as follows: the hybridoma cell of the present invention described later may be cultured under conditions suitable for expression of the monoclonal antibody of the present invention and the cultured product (e.g., culture supernatant) may be treated to purify the monoclonal antibody of the present invention produced in the hybridoma cell.

An antigen-binding fragment may be prepared in any known manner, e.g., by treating the fill-length antibody with an appropriate protease or by gene recombination technology.

Purification of the monoclonal antibody of the present invention may be accomplished by using known purification means such as salting out, gel filtration, ion exchange chromatography, affinity chromatography, etc.

5. Preparation of the Hybridoma Cell of the Present Invention

The hybridoma cell of the present invention may be actually prepared (established) as follows, without being limited thereto.

(1) Preparation of Antigen

As an antigen required to prepare the monoclonal antibody of the present invention, it is possible to use (i) an ebolavirus GP-containing virus-like particle (VLP), as shown in the Examples described later, (ii) an ebolavirus GP-producing cell or a cell fraction thereof, or a host cell transformed with ebolavirus GP-encoding DNA, i.e., a prokaryotic host cell (e.g., *E. coli*) or a eukaryotic host cell (e.g., an insect cell, a mammalian cell) transfected with the full-length ebolavirus GP-encoding cDNA or a partial fragment thereof in any known manner, or a protein expressed and purified therefrom as it is or as a fusion protein, or (iii) ebolavirus GP synthesized in a peptide synthesizer, etc.

Ebolavirus GPs from two or more species (i.e., two species, three species, four species or five species) are preferred for use as immunogens.

(2) Immunization of Animals and Preparation of Antibody-Producing Cells

Mice or rats at 3 to 20 weeks of age are immunized with an antigen prepared in the manner as shown in (1) to collect antibody-producing cells from their spleens, lymph nodes and/or peripheral blood. For immunization, the antigen is administered to the animals subcutaneously, intravenously or intraperitoneally. Administration of the antigen is repeated 3 to 7 times every 2 to 3 weeks after the first administration. At 5 to 10 days after each administration, blood is sampled from the fundus venous plexus and the serum of each sample is tested for its ability to react with the antigen by enzyme immunoassay [Enzyme Immunoassay (ELISA): published by Igaku-Shoin Ltd., Japan, 1976], etc. A mouse or rat whose serum shows a sufficient antibody titer against the antigen used for immunization is provided for use as a source of antibody-producing cells. For fusion between spleen cells and myeloma cells, spleens are excised from the immunized mice or rats at 3 to 4 days after the final administration of the antigen substance to collect their spleen cells. The spleens are minced in a serum-free basal medium (hereinafter referred to as washing medium) and centrifuged to collect the cells, followed by treatment with Tris-ammonium chloride buffer (pH 7.65) for 1 to 2 minutes to remove erythrocytes. The resulting cells are washed with the washing medium and then provided for use as spleen cells for fusion.

(3) Preparation of Myeloma Cells

As myeloma cells, established cells derived from mice are used. Examples include 8-azaguanine-resistant mouse (BALB/c) myeloma cell lines P3-X63Ag8-U1 (P3-U1) [Current Topics in Microbiology and Immunology-1, European J. Immunology 6, 511-519 (1976)], SP2/O-Ag14 (SP-2) [Nature 276, 269-270 (1978)], P3-X63-Ag8653 (653) [J. Immunology 123, 1548-1550 (1979)] and P3-X63-Ag8 (X63) [Nature 256, 495-497 (1975)], etc. These cell lines are subcultured in 8-azaguanine medium [RPMI-1640 medium containing L-glutamine (2 mM), 2-mercaptoethanol ($5\times10^{-5}$ M), penicillin and streptomycin (100 U/ml, 100 μg/ml) (hereinafter referred to as RPMI-1640 medium), which is further supplemented with 10% fetal calf serum (FCS)] to thereby ensure cell counts equal to or greater than 5×10' cells on the day of fusion.

(4) Cell Fusion

The antibody-producing cells immunized in (2) and the myeloma cells obtained in (3) are washed well with PBS and mixed together at a cell count ratio of antibody-producing cells to myeloma cells=2:1 to 10:1. After being collected, the cells are dissociated well and washed under stirring at 37° C. with polyethylene glycol-1,500 (PEG-1,500) (50% PEG-1,500 (WV) dissolved in 75 mM Hepes (pH 8.0)) in a volume of 0.2 to 1 ml per $10^8$ antibody-producing cells, followed by several additions of 20% FCS-containing RPMI-1640 medium in a volume of 1 to 2 ml every 1 to 2 minutes to give a total volume of 50 ml. After being collected, the cells are gently dissociated and suspended in 100 ml of HAT medium [normal medium supplemented with hypoxanthine ($10^{-4}$ M), thymidine ($1.5\times10^{-5}$ M) and aminopterin ($4\times10^{-7}$ M)]. This suspension is dispensed into 96-well culture plates in a volume of 150 μl/well and cultured in a 5% $CO_2$ incubator at 37° C. for 7 to 14 days. After culture, the culture supernatants are sampled and tested, for example, by using enzyme immunoassay described in (5) or FACS (which is an abbreviation of fluorescence-activated cell sorting) or the like to select an antibody which specifically reacts to ebolavirus GP from one or more species (i.e., one species, two species, three species, four species or five species). Alternatively, the culture supernatants are subjected to a neutralization test to select an antibody which shows neutralizing activity against one or more species (i.e., one species, two species, three species, four species or five species) of ebolavirus or a pseudotype virus enveloped with ebolavirus GP. Then, cloning is repeated twice by limiting dilution techniques to select a clone stably showing a strong antibody titer as a hybridoma line producing a monoclonal antibody which recognizes an internal fusion loop of ebolavirus GP.

Thus, in another related embodiment of the present invention, there is provided a method for producing the monoclonal antibody of the present invention, which comprises culturing the hybridoma cells and collecting the monoclonal antibody of the present invention from the resulting cultured product.

6. Medicament of the Present Invention

The monoclonal antibody of the present invention can be used as a medicament such as a prophylactic or therapeutic agent for Ebola virus disease. When used as a medicament, the monoclonal antibody compatible with humans or animal species in need of treatment or prevention of Ebola virus disease is used. When the medicament is used in humans, the monoclonal antibody of the present invention is preferably a human antibody, a humanized antibody, or a chimeric antibody such as a mouse-human chimeric antibody.

The term "Ebola virus disease" refers to a disease caused by infection with ebolavirus. Ebola virus disease develops after infection with ebolavirus and the subsequent incubation period. Early symptoms of Ebola virus disease are fatigue fever, myalgia, headache and sore throat, which are followed by vomiting, diarrhea, exanthema, renal and hepatic dysfunction, external hemorrhage and other symptoms.

A prophylactic or therapeutic agent comprising the monoclonal antibody of the present invention is less toxic and may be administered either directly as a solution or as a pharmaceutical composition in any suitable dosage form to a subject, e.g., humans or non-human mammals (e.g., rats, rabbits, sheep, pigs, cows, cats, dogs, monkeys), for example, by the parenteral route.

The monoclonal antibody of the present invention may be administered either alone or as a suitable pharmaceutical composition. The pharmaceutical composition used for administration may comprise the monoclonal antibody of the present invention or a salt thereof and a pharmacologically acceptable carrier, diluent or excipient. Such a pharmaceutical composition is provided in any dosage form suitable for parenteral administration.

For parenteral administration, for example, compositions such as injections and suppositories are used, and injections may encompass dosage forms such as intravenous injections, subcutaneous injections, intracutaneous injections, intramuscular injections, drip infusions, etc.

Such injections may be prepared in any known manner. For preparation of injections, for example, the monoclonal antibody of the present invention or a salt thereof may be dissolved, suspended or emulsified in a sterile aqueous or oil-based solution commonly used for injections. Examples of an injectable aqueous solution used for this purpose include physiological saline, an isotonic solution containing glucose and/or other auxiliary agents, and so on, which may be used in combination with an appropriate solubilizer such as an alcohol (e.g., ethanol), a polyalcohol (e.g., propylene glycol, polyethylene glycol), a nonionic surfactant (e.g., Polysorbate 80, HCO-50 (polyoxyethylene (50 mol) adduct of hydrogenated castor oil)), etc. Examples of an oil-based solution used for this purpose include sesame oil, soybean oil and so on, which may be used in combination with a solubilizer such as benzyl benzoate, benzyl alcohol, etc. The prepared injectable solutions are preferably filled into appropriate ampules. Suppositories for intrarectal administration may be prepared by mixing the monoclonal antibody of the present invention or a salt thereof with a base commonly used for suppositories.

Compositions for oral administration include solid or liquid dosage forms, more specifically tablets (including sugar-coated tablets and film-coated tablets), pills, granules, powders, capsules (including soft capsules), syrups, emulsions, suspensions and so on. Such compositions may be prepared in any known manner and may comprise carriers, diluents or excipients commonly used in the field of formulations. Examples of carriers and excipients used for tablets include lactose, starch, sucrose, and magnesium stearate.

The above parenteral or oral pharmaceutical compositions are advantageously formulated into unit dosage forms suited to the dose of the active ingredient. Examples of such unit dosage forms include tablets, pills, capsules, injections (ampules), and suppositories. The content of the monoclonal antibody is usually about 5 to 500 mg per unit dosage form. In particular, the above monoclonal antibody is preferably contained in an amount of about 5 to 100 mg for injections and about 10 to 250 mg for other dosage forms.

It should be noted that each composition described above may comprise an additional active ingredient as long as it does not cause any unwanted interaction when combined with the above monoclonal antibody.

The dose of a medicament containing the monoclonal antibody of the present invention will vary depending on the subject of administration, the target disease, symptoms, the route of administration, etc. For example, when used for prevention or treatment of Ebola virus disease in adults, the monoclonal antibody of the present invention is advantageously administered at a single dose of generally about 0.01 to 20 mg/kg body weight, preferably about 0.1 to 10 mg/kg body weight, more preferably about 0.1 to 5 mg/kg body weight, about once to five times a day, preferably about once to three times a day, by the intravenous route. For other cases of parenteral administration (e.g., subcutaneous administration) and oral administration, corresponding doses may be administered. If the symptoms are particularly severe, the dose may be increased depending on the symptoms.

The monoclonal antibody of the present invention may be formulated together with one or more additional prophylactic or therapeutic agents effective for prevention or treatment of ebolavirus, or alternatively, may be administered simultaneously or sequentially with such additional prophylactic or therapeutic agents. For example, the monoclonal antibody of the present invention may be administered as a cocktail formulation with one or more additional anti-ebolavirus antibodies binding to other epitopes different from the epitope for the antibody of the present invention, or alternatively, may be administered simultaneously or sequentially with such additional antibodies. Further, for use as one or more antibodies in the present invention, two or more of the therapeutic agents described above may be used in combination. Such a combination therapy allows a significant reduction in the probability of occurrence of escape virus.

Specific examples of an additional anti-ebolavirus antibody which can be used as a cocktail formulation with the monoclonal antibody of the present invention or administered simultaneously or sequentially in combination with the monoclonal antibody of the present invention include a monoclonal antibody against ebolavirus, 42/3.7 (Journal of Virology, 2003, 1069-1074; Vaccine, 2007, 25(6), 993-9) or a human-mouse chimeric monoclonal antibody against ebolavirus, ch133 or ch226 (PLoS ONE 7(4): e36192, 2012). Moreover, it is also possible to use human-type chimeric antibodies or humanized antibodies prepared from these antibodies on the basis of the amino acid sequences of their variable regions.

When these additional anti-ebolavirus antibodies and the monoclonal antibody of the present invention are used in combination or used as a cocktail formulation, a synergistic virus inhibitory effect can be obtained in the prevention or treatment of ebolavirus.

The medicament of the present invention may be provided in the form of a kit. In addition to the medicament of the present invention, such a kit may further comprise an additional active ingredient, an additional medicament, an instruction manual, a container, etc.

Moreover, the present invention provides a prophylactic or therapeutic method for Ebola virus disease, which comprises administering the monoclonal antibody of the present invention in a prophylactically or therapeutically effective amount to a subject in need of prevention or treatment of Ebola virus disease.

7. Diagnostic Reagent of the Present Invention

The monoclonal antibody of the present invention is useful in a diagnostic reagent or diagnostic method for Ebola virus disease (hereinafter referred to as "the diagnostic reagent of the present invention"). For use in a diagnostic reagent or diagnostic method, the monoclonal antibody of the present invention is preferably an IgG1 or IgG2 antibody comprising light chain and heavy chain variable regions of mouse origin, and γ1 heavy chain and κ light chain constant regions of mouse origin.

For detection of ebolavirus, the monoclonal antibody of the present invention may be actually reacted with a biological sample to detect signals from the reacted antibody. Signals from the antibody serve as an indicator of the amount of ebolavirus in the biological sample.

The biological sample is not limited in any way as long as it is suspected of containing ebolavirus, and examples include whole blood, serum, plasma, lymphocyte culture supernatant, urine, spinal fluid, saliva, sweat, ascites, amniotic fluid, a cell or organ extract, etc.

A subject from which the biological sample is to be taken is not limited in any way as long as it is suspected of being infected with ebolavirus, and includes humans or non-human mammals (e.g., rats, rabbits, sheep, pigs, cows, cats, dogs, monkeys).

For detection of ebolavirus using the monoclonal antibody of the present invention, a biological sample taken as an analyte from a subject and the monoclonal antibody of the present invention are bound to each other through antigen-antibody reaction, and the amount of the target antigen in the sample is measured on the basis of the amount of the antibody bound thereto. The antigen amount may be detected according to any known immunological assay, and immunoprecipitation, immunoagglutination, labeling immunoassay, immunonephelometry, Western blotting, flow cytometry and so on may be used, for example. In the case of labeling immunoassay, signals from the antibody may be expressed as the labeled amount which is directly detected with a labeling antibody, or alternatively, may be expressed relative to an antibody of known concentration or of known titer, which is used as a standard solution. Namely, such a standard solution and an analyte are measured with a meter, and antibody signals in the sample may be expressed as a relative value based on the value of the standard solution.

Examples of labeling immunoassay include ELISA assay, EIA assay, RIA assay, fluorescence immunoassay (FIA), chemiluminescence immunoassay and so on. In particular, ELISA assay is preferred in terms of simplicity and high sensitivity.

Further, the detection results thus obtained can be used to evaluate or diagnose the presence or absence of ebolavirus infection. For example, a biological sample from which ebolavirus was detected is determined as ebolavirus infection positive, while a biological sample from which ebolavirus was not detected is determined as ebolavirus infection negative, and a positive case is determined to be suspected of developing Ebola virus disease, whereby the status of Ebola virus disease can be evaluated.

The status of Ebola virus disease is intended to mean the presence or absence of Ebola virus disease or the progress thereof.

The monoclonal antibody of the present invention may be provided in the form of a diagnostic kit for Ebola virus disease (hereinafter referred to as "the kit of the present invention"). The kit of the present invention may be used for diagnosis or treatment of Ebola virus disease. The kit of the present invention comprises the monoclonal antibody of the present invention, and may further comprise a labeling substance, or alternatively, an immobilized reagent in which the antibody or a labeled product thereof is immobilized. The labeled product of the antibody is intended to mean the antibody labeled with an enzyme, a radioisotope, a fluorescent compound, a chemiluminescent compound or the like. In addition to the above constituent elements, the kit of the present invention may further comprise other reagents required to accomplish ebolavirus detection using the monoclonal antibody of the present invention, for example, an enzyme substrate (e.g., a chromogenic substrate), an enzyme substrate diluent, an enzyme reaction stop solution, or an analyte diluent and so on when the labeled product is an enzymatically labeled product.

It should be noted that all publications, patent application publications, patent gazettes and other patent documents cited herein, are incorporated herein by reference.

EXAMPLES

The present invention will be further described in more detail by way of the following illustrative examples, which are not intended to limit the scope of the present invention.

Example 1

Preparation of Mouse Monoclonal Antibody (1) Preparation of Immunogens

Virus-like particles (VLPs) containing Zaire and Sudan ebolavirus GPs were created as immunogens.

In more detail, these VLPs were created as follows. Genes for Zaire or Sudan ebolavirus GP, VP40 and NP were each integrated into a protein expression vector for animal cells, pCAGGS, to thereby construct plasmids, which were then transfected into SV40 large T antigen-expressing human embryonic kidney cells (HEK293T cells). The transfected cells were cultured at 37° C. in a 5% $CO_2$ incubator for 48 hours, and the supernatant was then collected and centrifuged at 3500 rpm for 15 minutes. The resulting supernatant was subjected to ultracentrifugation at 4° C. at 28000 rpm for 2 hours using a 25% sucrose solution as a cushion, and the supernatant was removed off and the residue was resuspended by addition of PBS. After 24 hours, the VLP-containing resuspension was overlaid on a sucrose solution in which a density gradient has been established, followed by ultracentrifugation at 28000 rpm at 4° C. for 2 hours. A solution was collected from a fraction showing a VLP-containing band, and then diluted with PBS and subjected again to ultracentrifugation at 4° C. at 28000 rpm for 2 hours. Then, the supernatant was removed off and VLPs were resuspended with a small amount of PBS. After 24 hours, VLPs were collected and adjusted to a protein concentration of 1 mg/ml. The created VLPs have GP on their surface, are lined with VP40 and incorporate NP in their interior.

(2) Preparation of Hybridoma

Mice administered with rapamycin were immunized three times with Zaire ebolavirus VLPs and once with Sudan ebolavirus VLPs. At 3 days after the final immunization with Zaire ebolavirus VLPs, their spleens were excised and fused with myeloma cells (P3U1) to create a monoclonal antibody-producing hybridoma in a standard manner.

In more detail, the hybridoma was created as follows. Five BALB/c mice at 15 weeks of age were intraperitoneally administered with 75 µg/kg of rapamycin (Wako Pure Chemical Industries, Ltd., Japan) on a daily basis starting from 1 week before initiation of immunization until the date at which their spleens were excised. 100 µg of Zaire ebolavirus VLPs was intraperitoneally administered three times at intervals of 2 or 3 weeks. At 1 week after the third immunization, serum was sampled from each mouse and subjected to a neutralization test. At 5 weeks after the third immunization, two mice found to have cross-neutralizing activity among ebolavirus species were intraperitoneally administered with 100 µg of Sudan ebolavirus VLPs, followed by a neutralization test after 1 week. One mouse found to have high neutralizing activity against Zaire ebolavirus and also have neutralizing activity against the other ebolavirus species was selected and intraperitoneally administered with 100 µg of Zaire ebolavirus VLPs at 2 weeks after the fourth immunization. At 3 days after the final immunization, the spleen was excised from the mouse, and spleen cells were dissociated in PBS and then centrifuged at 1700 rpm for 6 minutes. The supernatant was removed off, and the cells were washed three times with 25 ml of PBS. P3U1 cells were cultured in 10% FBS-containing RPMI-1640 medium and centrifuged at 1300 rpm for 3 minutes. Then, the supernatant was removed off and the cells were resuspended with 25 ml of PBS. To the immunized spleen cells, the P3U1 suspension was added at a cell count ratio of the immunized spleen cells to the myeloma cells=2:1 to 5:1. After centrifugation at 1300 rpm for 5 minutes, the supernatant was removed off. The cells were dissociated well and 1 ml of PEG 1500 (Roche Diagnostics) was then added thereto at 37° C. over 1 minute. After being mixed gently, the cells were allowed to stand for 1 minute. To this cell suspension, 20% FCS-containing RPMI-1640 medium (GIBCO, Life Technologies) which had been warmed to 37° C. was added several times in a volume of 1 to 2 ml, and was further slowly added to give a total volume of 50 ml. After being collected by centrifugation, the cells were gently dissociated and suspended in 250 ml of 20% FCS-containing RPMI-1640 medium supplemented with HAT Supplement (GIBCO, Life Technologies). This suspension was dispensed into 96-well plates in a volume of 150 µl/well and cultured in a 5% $CO_2$ incubator at 37° C. for 7 to 14 days, during which half of the medium was replaced with fresh medium every 2 or 3 days. The supernatants of the grown hybridomas were used for screening (described later) to select an antibody neutralizing all the ebolavirus species, and cloning was repeated twice by limiting dilution techniques. The thus obtained mouse monoclonal antibody 6D6-producing hybridomas were grown in 20% FBS-containing RPMI-1640 medium and then acclimated in 10% FBS-containing RPMI-1640 medium and cultured therein.

(3) Antibody Screening

Figures 1, 5:
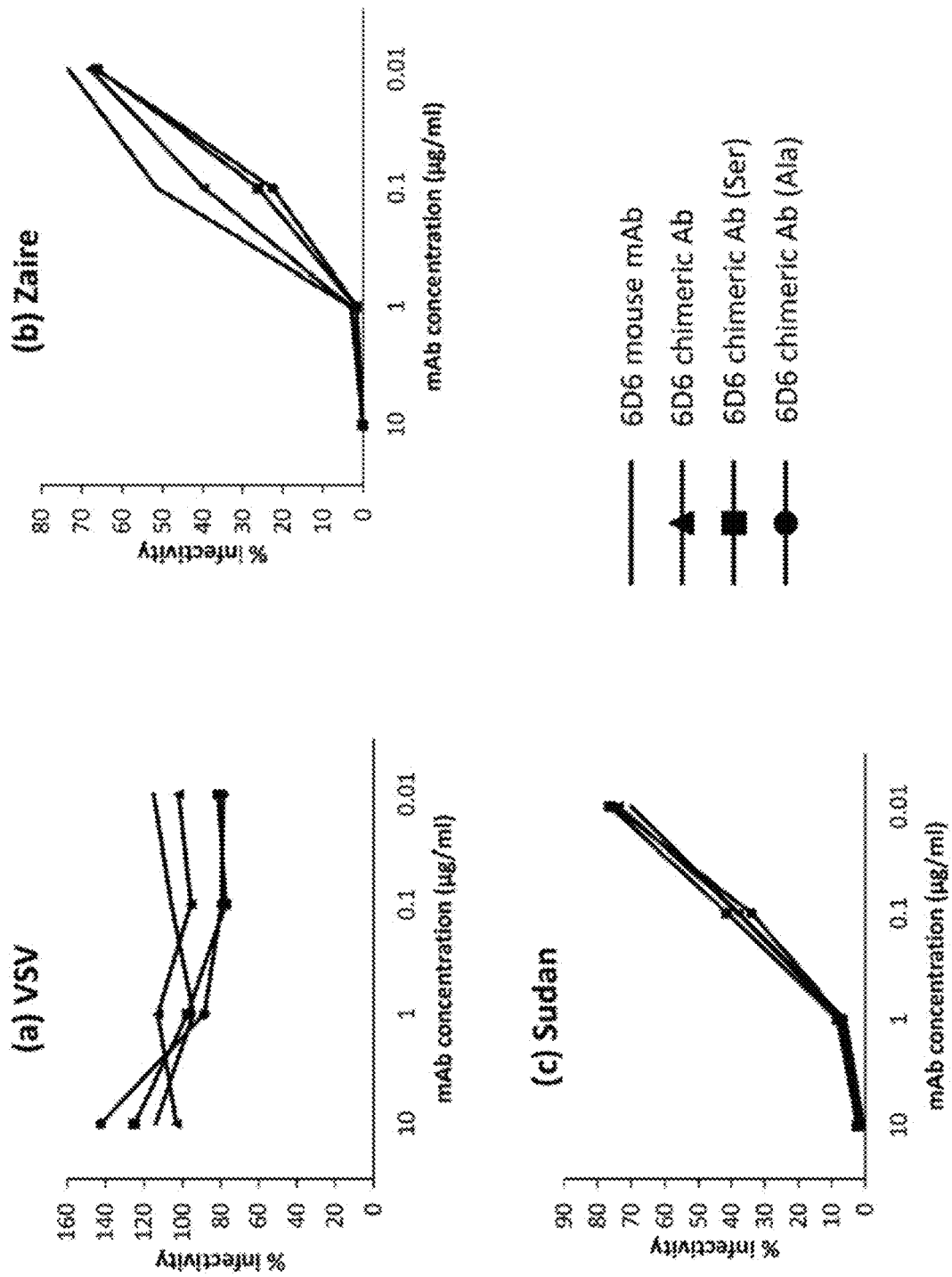

The culture supernatants of hybridomas were screened for neutralizing activity against replication-incompetent pseudotype vesicular stomatitis virus (VSV) enveloped with ebolavirus GP (FIG. 1 (A)) to obtain an antibody neutralizing all the ebolavirus species.

In more detail, the antibody neutralizing all the ebolavirus species was selected as follows. Replication-incompetent pseudotype vesicular stomatitis virus enveloped with Zaire ebolavirus GP (VSV-Zaire GP) was dispensed into 96-well plates in a volume of 60 µl/well, to which the culture supernatants of individual hybridomas were then added in 60 µl volumes and mixed. As a control, the culture solution (60 µl) was used. After 30 to 60 minutes, Vero E6 cells which had been cultured in 96-well plates from the day before were inoculated with these virus-culture supernatant mixtures in 100 µl volumes and cultured in a 5% $CO_2$ incubator at 37° C. for 18 to 24 hours. After culture, the wells were measured for infectivity titer using GFP as an indicator in an In Cell Analyzer 2000 to select wells showing 80% or more neutralization when compared to the control. The cells from the selected wells were cultured, and their culture supernatants were used to conduct a neutralization test against Sudan ebolavirus, Bundibugyo ebolavirus, Tai Forest ebolavirus or Reston ebolavirus in the same manner as shown in the neutralization test against VSV-Zaire GP to thereby select a well showing 80% or more neutralization against all the species when compared to the control.

This pseudotype VSV system is widely used in screening for neutralizing activity of antibodies (Takada A, et al., A system for functional analysis of Ebola virus glycoprotein. Proc Natl Acad Sci USA 94:14764-9, 1997).

Figures 2, 5:
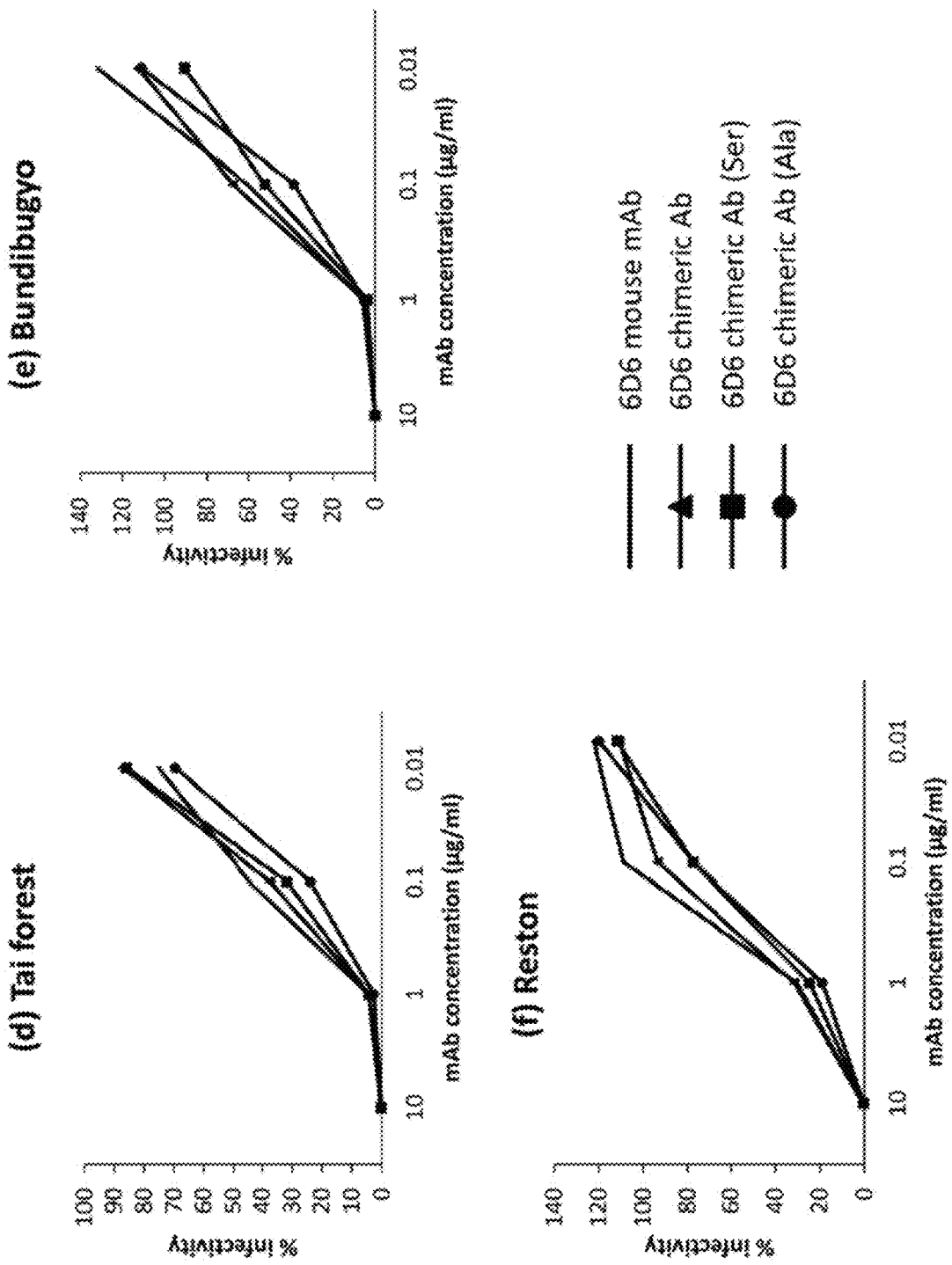
Figure 7:
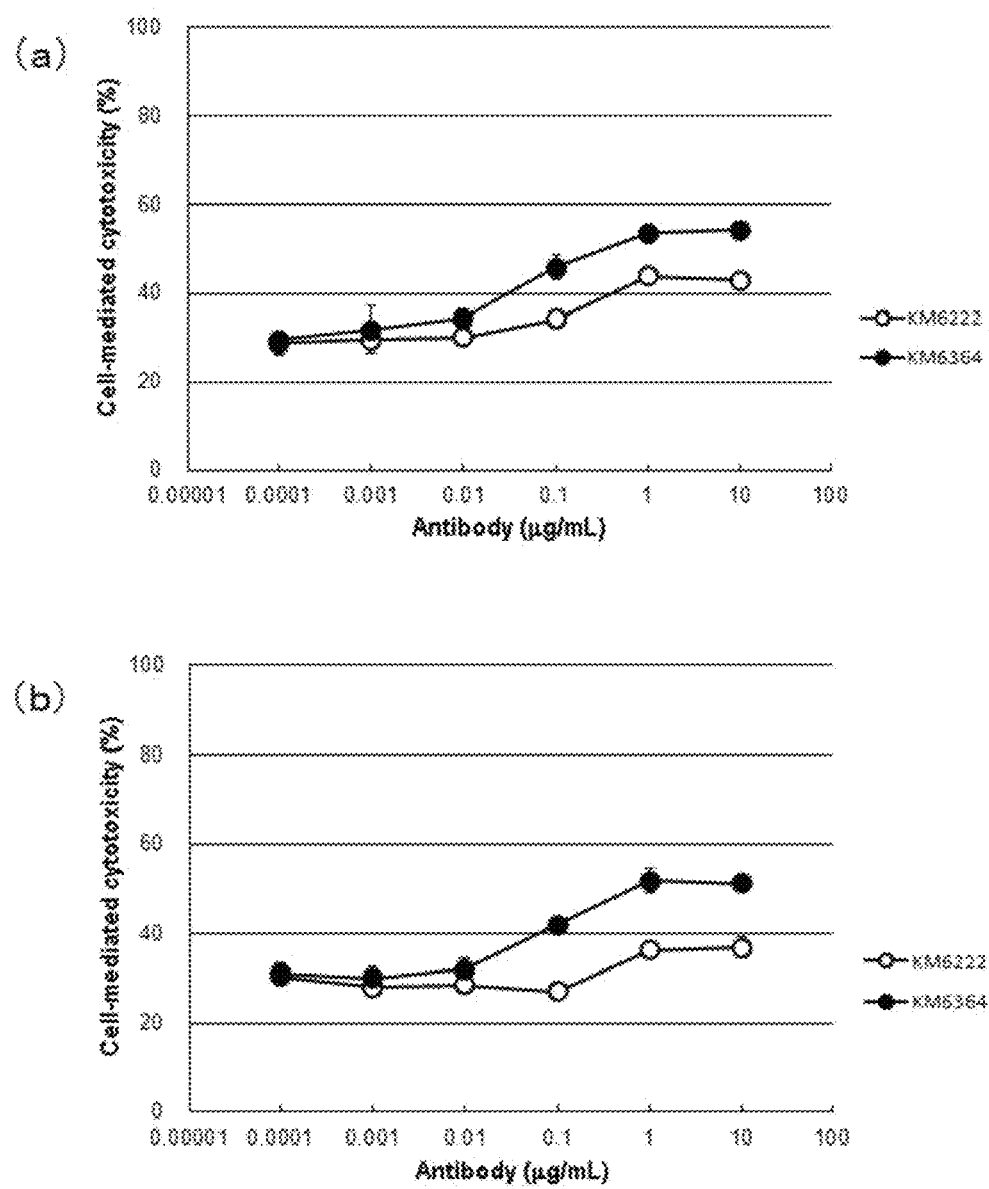
FIG. 7 shows the results obtained when anti-Ebola antibodies KM6222 and KM6364 were measured for their cell-mediated cytotoxicity using effector cell suspensions derived from PBMCs isolated from the peripheral blood of two normal subjects. The horizontal axis represents antibody concentration (μg/mL) and the vertical axis represents cell-mediated cytotoxicity (%).

Screening of about 1500 clones resulted in a mouse monoclonal antibody (6D6) binding to all the known ebolavirus GPs and thereby efficiently neutralizing virus infectivity (FIG. 2).

(4) Purification of Monoclonal Antibody and Measurement of Neutralizing Activity Pristine-treated BALB/c mice were intraperitoneally administered with the 6D16-producing hybridoma in an amount of $5 \times 10^6$ cells per animal. After 7 to 10 days, ascites were collected from mice with enlarged abdomen and centrifuged at 3000 rpm for 15 minutes to remove blood cell components. The antibody was purified from the ascites in accordance with the manufacturer's instructions attached to an Affi-Gel Protein A MAPS II Kit (BIO-RAD). The isotype of 6D6 antibody was identified as IgG1, κ chain as a result of determination with a MOUSE ISOTYPING KIT (AbD Serotec).

The purified antibody was measured for its 50% inhibitory concentration ($IC_{50}$) by a virus infectivity neutralization test using the pseudotype VSV system and Vero cells. As a result, the $IC_{50}$ values against Zaire ebolavirus, Sudan ebolavirus, Tai Forest ebolavirus, Bundibugyo ebolavirus and Reston ebolavirus were 0.12, 0.19, 0.33, 0.24 and 0.62 µg/ml, respectively.

Example 2

Confirmation of Binding Site

Replication-competent pseudotype VSV with Zaire ebolavirus GP (FIG. 1 (B)) was cultured in the presence of the antibody to select escape mutants, which were then compared for the amino acid sequence of GP with their parent strain.

In more detail, creation of replication-competent pseudotype VSV with Zaire ebolavirus GP, selection of escape mutants, and comparison of the amino acid sequence of GP were accomplished as follows. pATX-VSVdeltaG+ MCS lacking VSV G in the entire genome of VSV was used to prepare an expression plasmid carrying Zaire ebolavirus GP integrated in place of this G site. This plasmid and pbl plasmids carrying the VSV N, P, M and L genes, respectively, were simultaneously transfected into Syrian hamster kidney cells (BHK-T7) constitutively expressing T7 RNA polymerase. After 3 days, cell culture supernatants were collected from wells showing a cytopathogenic effect (CPE). From the collected culture supernatants, virus RNA was extracted in accordance with the manufacturer's instructions attached to a QIAamp Viral RNA Mini Kit (QIAGEN) and then confirmed for the gene of Zaire ebolavirus GP contained in the genes of the thus created replication-competent pseudotype VSV, along with its amino acid sequence (parent strain). The thus created replication-competent pseudotype VSV with Zaire ebolavirus GP was inoculated into Vero E6 cells and allowed to replicate therein. The thus replicated replication-competent pseudotype VSV with Zaire ebolavirus GP was dispensed and stocked at −80° C. This replication-competent pseudotype VSV with Zaire ebolavirus GP and 6D6 were mixed together and reacted for 1 hour at room temperature, and then inoculated into Vero E6 cells without supernatant. After adsorption in a 5% $CO_2$ incubator at 37° C. for 1 hour, the cells were washed once with a serum-free medium and overlaid with a culture solution containing 6D6 (10 µg/ml) and 0.8% agar. After culture in a 5% $CO_2$ incubator at 37° C. for 48 hours, viruses were collected from the formed plaques and their extracted RNA extracts were used to decode the nucleotide sequence of their GP gene. The deduced amino acid sequence was compared between escape mutants and their parent strain. Mutated amino acids were identified to estimate an epitope for 6D6.

The escape mutants showed a nucleotide substitution resulting in an amino acid mutation (i.e., a mutation at position 528 from glycine to arginine or glutamic acid) in their GP gene, and this amino acid was found to be located in a region essential for GP-mediated membrane fusion (i.e., an internal fusion loop) on the three-dimensional structure of GP, whereby the epitope for 6D6 was estimated to be present on an internal fusion loop (FIG. 3).

The amino acid sequence of an internal fusion loop of GP is shown in SEQ ID NO: 1, SEQ ID NO: 2, SEQ ID NO: 3, SEQ ID NO: 4 and SEQ ID NO: 5 for Zaire ebolavirus, Sudan ebolavirus, Bundibugyo ebolavirus, Tai Forest ebolavirus and Reston ebolavirus, respectively. Likewise, the amino acid sequence of an internal fusion loop is shown in SEQ ID NO: 6, SEQ ID NO: 7, SEQ ID NO: 8 and SEQ ID NO: 9 for Zaire ebolavirus escape mutant strain [5 clones among 6 clones], Zaire ebolavirus escape mutant strain [1 clone among 6 clones], Reston ebolavirus escape mutant strain [2 clones among 6 clones] and Reston ebolavirus escape mutant strain [4 clones among 6 clones], respectively.

Example 3

Gene Sequence Determination for Mouse Monoclonal Antibody 6D6

Gene sequences encoding the full-length 6136 antibody and variable regions thereof were cloned to decode their nucleotide sequences.

In more detail, gene sequence cloning and nucleotide sequence decoding were accomplished as follows. The 6D6-producing hybridoma was cultured in a 10% fetal calf serum-containing RPMI 1640 medium in the presence of 5% $CO_2$ at 37° C. for 3 to 4 days. From $5 \times 10^6$ to $1 \times 10^7$ cells of the hybridoma, mRNA was extracted using an RNAeasy Mini kit (QIAGEN) in accordance with the manufacturer's instructions attached thereto. cDNAs for the antibody variable region genes were each synthesized by 5'-RACE using a Gene Racer Kit (Invitrogen), amplified by PCR, inserted into a pCR-Blunt II-TOPO cloning vector (Life Technologies) and then transformed into E. coli. The antibody constant region genes were each amplified using an OneStep RT-PCR Kit (QIAGEN), inserted into a TOPO TA Cloning vector (Life Technologies) and then transformed into E. coli. After overnight culture at 37° C., the plasmid was extracted from each of the grown colonies and its nucleotide sequence was decoded using M13 forward primer and M13 reverse primer included in the cloning kit. To obtain full-length antibody gene sequences for heavy and light chains, the variable region and constant region genes were ligated together for each chain.

Based on the gene encoding the full-length antibody and gene sequences encoding the VH and VL regions, amino acid sequences were determined for the full-length 6D6 antibody and variable regions thereof. The amino acid sequences of the 6D6 light and heavy chains are shown in SEQ ID NOs: 24 and 25, respectively. The amino acid sequences of the 6D6 VL and VH regions are shown in SEQ ID NOs: 10 and 11, respectively.

Moreover, the amino acid sequences of CDRs were determined by being compared with known antibody amino acid sequences according to the CDR definition (http://www.bioinf.org.uk/abs/#cdrid).

The results obtained are shown in FIG. 4. In addition, the amino acid sequences of CDRL1, CDRL2 and CDRL3 are shown in SEQ ID NO: 12, SEQ ID NO: 13 and SEQ ID NO: 14, respectively. The amino acid sequences of CDRH1, CDRH2 and CDRH3 according to the definition of Kabat are shown in SEQ ID NO: 15, SEQ ID NO: 16 and SEQ ID NO: 17, respectively. The amino acid sequences of CDRH1, CDRH2 and CDRH3 according to the definition of AbM are shown in SEQ ID NO: 18, SEQ ID NO: 19 and SEQ ID NO: 20, respectively. The amino acid sequences of CDRH1, CDRH2 and CDRH3 according to the definition of Chothia are shown in SEQ ID NO: 21, SEQ ID NO: 22 and SEQ ID NO: 23, respectively.

Example 4

Preparation of 6D6 Chimeric Antibody (1) Construction of 606 Chimeric Antibody Expression Vectors The chimeric antibodies to be prepared in the present invention are a 6D6 chimeric antibody designed such that the amino acid sequences of VH and VL of the mouse monoclonal antibody 6D6 obtained in Example 1 are linked to the amino acid sequences of the H chain constant region of the human IgG1 disclosed in WO97/10354 and the human κ chain constant region, respectively, as well as a chimeric antibody designed to comprise an Ala or Ser residue substituted for the Cys residue contained in VH CDR3 of this 6D6 chimeric antibody (the amino acid sequence of CDR3 is shown in SEQ ID NO: 40 or 41).

First, DNA fragments encoding VH and VL of the mouse monoclonal antibody 6D6 obtained in Example 1 and an amino acid sequence having Ala or Ser substituted for the Cys residue contained in VH CDR3 were each inserted into a vector (hereinafter referred to as a transposon vector) comprising the neomycin resistance gene and the cycloheximide (CHX) resistance gene in place of the drug resistance genes in the Tol2 transposon vector appearing in WO2010/143698 and comprising DNA encoding the amino acid sequence of the human constant region or the human κ chain constant region, thereby preparing 6D6 chimeric antibody expression vectors.

A pCR vector comprising a DNA fragment encoding VL of the mouse monoclonal antibody 6D6 was used as a template for PCR with 6D6L-F1 and 6D6L-R1 (SEQ ID NOs: 26 and 27), and the resulting PCR product was then used as a template for PCR with 6D6L-F2 and 6D6L-R2 (SEQ ID NOs: 28 and 29), whereby the DNA fragment encoding VL was amplified. A DNA fragment encoding VH of the mouse monoclonal antibody 6D6 was prepared by total synthesis.

For preparation of a 6D6 chimeric antibody L chain expression vector, a transposon vector carrying the human κ chain constant region was digested with restriction enzymes SalI (New England Biolabs) and BsiWI (New England Biolabs), and a DNA fragment encoding VL was then inserted at an appropriate position of the transposon vector.

For preparation of a 6D6 chimeric antibody H chain expression vector, a transposon vector carrying the H chain constant region of human IgG1 was digested with restriction enzymes SalI (New England Biolabs) and ApaI (New England Biolabs), and a DNA fragment encoding VH was then inserted at an appropriate position of the transposon vector.

For preparation of an H chain expression vector for the antibody comprising Ala substituted for the Cys residue contained in VH CDR3 of the 6D6 chimeric antibody, the 6D6 chimeric antibody H chain expression vector was used as a template for PCR with 6D6H-Avr-F and 6D6H-Mut-Ala-R (SEQ ID NOs: 30 and 31) and with 6D6H-Mut-Ala-F and 6D6H-Apa-R (SEQ ID NOs: 32 and 33), and the resulting PCR product was inserted at an appropriate position of the 6D6 chimeric antibody H chain expression vector digested with restriction enzymes AvrII (New England Biolabs) and ApaI (New England Biolabs).

For preparation of an H chain expression vector for the antibody comprising Ser substituted for the Cys residue contained in VH CDR3 of the 6D6 chimeric antibody, the same procedure as shown above was repeated using primers 6D6H-Avr-F and 6D6H-Mut-Ser-R (SEQ ID NOs: 30 and 34) and primers 6D6H-Mut-Ser-F and 6D6H-Apa-R (SEQ ID NOs: 35 and 33) to insert the resulting PCR product at an appropriate position of the 6D6 chimeric antibody H chain expression vector.

(2) Expression and Purification of 6D6 Chimeric Antibodies Using Animal Cells

The 6D6 chimeric antibody expression vectors prepared in Example 4(1) above were each transiently transfected into Expi293F cells, and these cells were cultured in Expi293™ Expression Medium (Life Technologies) for 3 to 6 days, followed by collection of their culture supernatant to purify each 6D6 chimeric antibody in the following manner.

The culture supernatants were each centrifuged under conditions of 3000 rpm and 4° C. for 20 minutes to collect the supernatant, which was then filtered through a PES membrane of 0.2 μm pore size (Thermo). A column of 0.8 cm diameter was filled with 0.5 mL of Mab Select Sure (Amersham Pharmacia Biotech), added with 5 mL of purified water and then equilibrated with 5 mL of 0.15 M citrate buffer (pH 3.5) and 5 mL of 0.2 M sodium borate-0.15 M NaCl buffer (pH 7.5) (hereinafter referred to as borate buffer).

Then, the above culture supernatants were each passed through the column, followed by washing with 5 mL of borate buffer and 5 mL of 0.15 M citric acid (pH5.0). After washing, 2.25 mL of 0.1 M citrate buffer (pH 3.5) was used to elute proteins adsorbed onto the carrier. Elution fractions were obtained in two ways, i.e., as fractions of 250 μL volume and fractions of 2 mL volume. Then, the resulting fractions were each measured for absorbance at 280 nm ($OD_{280}$) with an absorptiometer (NanoDrop) to identify an elution fraction containing a desired protein.

The elution fraction containing a desired protein was subjected to buffer replacement with DPBS (pH 7.0) (Gibco) through NAP-25 (GE Healthcare). The resulting antibody solution was sterilized by filtration through Millex GV of 0.22 μm pore size (MILLIPORE) and stored at 4° C.

As a result of SDS-PAGE electrophoresis on the purified proteins, bands were confirmed for the desired H chain of about 50 kDa and the desired L, chain of about 25 kDa, thus confirming that purified antibodies were obtained for 6D6 chimeric antibody, 61D6 chimeric antibody (Ala) and 6D6 chimeric antibody (Ser).

Example 5

Activity Evaluation of 6D6 Chimeric Antibodies

The 6D6 chimeric antibody and the chimeric antibody comprising Ser or Ala substituted for the Cys residue contained in H chain CDR3, each being prepared in Example 4, were measured for their binding activity by ELISA assay using VLP as an antigen. As a result, these 6D6 chimeric antibodies were each confirmed to have the same binding activity to all the ebolavirus species as the mouse monoclonal antibody 6D6.

Likewise, when measured for their neutralizing activity in the same manner as shown above using the pseudotype VSV system and Vero cells, these 6D6 chimeric antibodies were each confirmed to have the same neutralizing activity against all the ebolavirus species as the mouse monoclonal antibody 6D6 (FIG. 5). Moreover, each antibody was found to achieve nearly complete inhibition of infection with Zaire, Sudan, Tai Forest and Bundibugyo ebolaviruses at an antibody concentration of 1 μg/mL. Furthermore, each antibody was also found to achieve complete inhibition of infection with all the five ebolavirus species including Reston ebolavirus at an antibody concentration of 10 μg/mL.

The foregoing results suggested that the antibodies of the present invention would show a broad viral spectrum allowing reaction with all the existing ebolaviruses and therefore have a high infection inhibitory effect, when compared to existing anti-ebolavirus antibodies.

Example 6

Activity Evaluation of 6D6 Chimeric Antibodies for Antibody-dependent Cell-mediated Cytotoxicity (ADCC) Against Membrane-bound GP Antigen-expressing Cell Lines 6D6 chimeric antibodies were measured for ADCC activity against membrane-bound GP antigen-expressing cell lines in accordance with the procedures shown below.

(1) Stable Expression and Purification of 6D6 Chimeric Antibodies Using CHO Cell Lines The expression vector prepared in Example 4 for an antibody comprising Ser substituted for the Cys residue contained in H chain CDR3 of the 6D6 chimeric antibody was transfected into animal cell lines in a standard manner [Antibody Engineering. A Practical Guide, W. H. Freeman and Company (1992)] to thereby obtain transformed cell lines stably expressing 6D6 chimeric antibodies. The CHO cell lines used were a CHO-K1 cell line and a CHO-K1 cell line wherein α1,6-fucosyltransferase (FUT8) gene was knocked out (hereinafter referred to as FUT8-knockout CHO-K1 cell line). The resulting transformed cell lines were each cultured for 10 to 14 days using BalanCD™ CHO Growth A medium and BalanCD™ CHO Feed I medium (Irvine Scientific), and the culture supernatants were collected in the same manner as shown in Example 4(2) for antibody purification. The collected antibody solutions were subjected to buffer replacement with 10 mmol/L sodium glutamate, 262 mmol/L D-sorbitol and 0.05 mg/mL Polysorbate 80 (pH 5.6), and then sterilized by filtration through Millex GV of 0.22 μm pore size (MILLIPORE) and store at 4° C. The antibodies obtained from the transformed cell lines derived from CHO-K1 and FUT8-knockout CHO-K1 cell lines are designated as KM6222 and KM6364, respectively.

(2) Preparation of Anti-Dinitrophenol (DNP) Chimeric Antibodies

For use as an isotype control antibody of the 6D6 chimeric antibody, anti-DNP mouse monoclonal antibody mDNP-1 (VL U16688, VH U116687) (Mol Immunol. 1996 June; 33(9):759-68) was used to prepare a human-type chimeric antibody thereof (hereinafter referred to as anti-DNP chimeric antibody) in the same manner as shown in Example 4. Stable expression and purification of the anti-DNP chimeric antibody using CHO cell lines were accomplished in the same manner as shown in Example 6(1). The antibodies obtained from the transformed cell lines derived from CHO-K1 and FUT8-knockout CHO-K1 cell lines are designated as KM8804 and KM8805, respectively.

(3) Measurement of Fucose Content in 6D6 Chimeric Antibodies and Anti-DNP Chimeric Antibodies In accordance with the procedures described in WO2002/31140, the 6D6 chimeric antibodies KM6222 and KM6364 as well as the anti-DNP chimeric antibodies KM8804 and KM8805 were examined for the percentage of fucose-free sugar chains in their N-linked complex sugar chains. The results obtained are shown in Table 1.

TABLE 1

| Fucose content measured for each antibody | |
|---|---|
| | Fucose content in N-linked complex sugar chains |
| KM6222 | 94% |
| KM6364 | 0% |
| KM8804 | 98% |
| KM8805 | 0% |

The results shown in Table 1 confirmed that the 6D6 chimeric antibody KM6364 and the anti-DNP chimeric antibody KM8805, each being prepared in FUT8-knockout CHO-K1 cells, had no fucose.

(4) Preparation of Target Cell Suspension

For preparation of a membrane-bound GP antigen-expressing cell line, the Zaire ebolavirus GP gene was integrated into a protein expression vector for animal cells, pCAGGS, and the thus constructed plasmid was transfected into SV40 large T antigen-expressing human embryonic kidney cells (HEK293T cells) in the same manner as shown in Example 1(1). The thus prepared membrane-bound GP antigen-expressing cell line was washed with phenol red-free RPMI 1640 medium (Life Technologies) containing 5% fetal bovine serum (FBS) (Life Technologies) (hereinafter referred to as ADCC medium) and adjusted with the same medium to an optimal cell density for use as a target cell suspension.

(5) Preparation of Effector Cell Suspensions

Peripheral blood mononuclear cells (PBMCs) were separated from the peripheral blood of two normal subjects to prepare effector cell suspensions (a) and (b) as described below. Using a syringe containing 0.5 mL of heparin sodium injection (Ajinomoto Co., Inc., Japan), peripheral blood (50 mL) was collected from each of two normal subjects. The collected peripheral blood was diluted with an equal volume of physiological saline (Otsuka Pharmaceutical Co., Ltd., Japan) and stirred well. Lymphoprep (Alere Technologies) was dispensed in 4.5 mL volumes into 15 mL tubes (Corning) and 10 mL of the diluted peripheral blood was gently overlaid thereon, followed by centrifugation under conditions of 840 g, brake off and room temperature for 20 minutes to separate a mononuclear cell layer. The resulting mononuclear cell fraction was washed twice with the ADCC medium and adjusted with the same medium to an optimal cell density for use as an effector cell suspension (a) or (b).

(6) Measurement of ADCC Activity

Into individual wells of 96-well U-bottom plates (FALCON), antibody solutions prepared from each antibody by 10-fold serial dilution starting from 30 μg/mL were dispensed in 50 μL volumes, and the target cell suspension prepared in Example 6(4) was then dispensed at $2\times10^4$ cells/50 μL/well, and finally the effector cell suspension prepared in Example 6(5) was dispensed at 2×10 cells/50 μL/well to give a total volume of 150 μL, followed by reaction at 37° C. for 4 hours. The ratio of effector cells (E) to target cells (T) in this system was set to 10:1. In the prepared membrane-bound GP antigen-expressing cell line, the GP-positive fraction was found to constitute about 50%, as analyzed by FCM; and hence the respective cell suspensions were dispensed at a substantial E/f ratio of 20:1. After the reaction, LDH Cytotoxic Test (Wako Pure Chemical Industries, Ltd., Japan) was used to measure color development in each culture supernatant. Cell-mediated cytotoxicity was determined according to the following equation.

$$\text{Cell-mediated cytotoxicity (\%)}=\{([\text{analyte absorbance}]-[\text{target cell spontaneous absorbance}]-[\text{effector cell spontaneous absorbance}])/([\text{target cell total absorbance}]-[\text{target cell spontaneous absorbance}])\}\times100 \qquad \text{(Equation)}$$

With regard to the cell-mediated cytotoxicity measured using the effector cell suspensions (a) and (b), the results obtained for the anti-DNP antibodies KM8804 and KM8805 are shown in FIG. 6 (*a*) and (*b*), while the results obtained for the anti-Ebola antibodies KM6222 and KM6364 are shown in FIG. 7 (*a*) and (*b*).

As shown in FIGS. 6 and 7, even under conditions where the isotype control antibodies KM8804 and KM8805 induce no cell-mediated cytotoxicity against the membrane-bound GP-expressing cell line, KM6222 and KM6364 were found to show antibody concentration-dependent ADCC activity against the membrane-bound GP-expressing cell line. Further, KM6364, which is an anti-Ebola antibody with enhanced ADCC activity, was found to have higher ADCC activity than KM6222 against the membrane-bound GP-expressing cell line.

Example 7

Neutralizing Activity Evaluation of 6D6 Chimeric Antibody with Enhanced ADCC Activity Using the 6D6 chimeric antibody KM6222 and the 6D6 chimeric antibody KM6364 with enhanced ADCC activity obtained in Example 6, their neutralizing activity was measured in the same manner as shown in Example 1(4) using the pseudotype VSV system and Vero cells.

Figure 8:
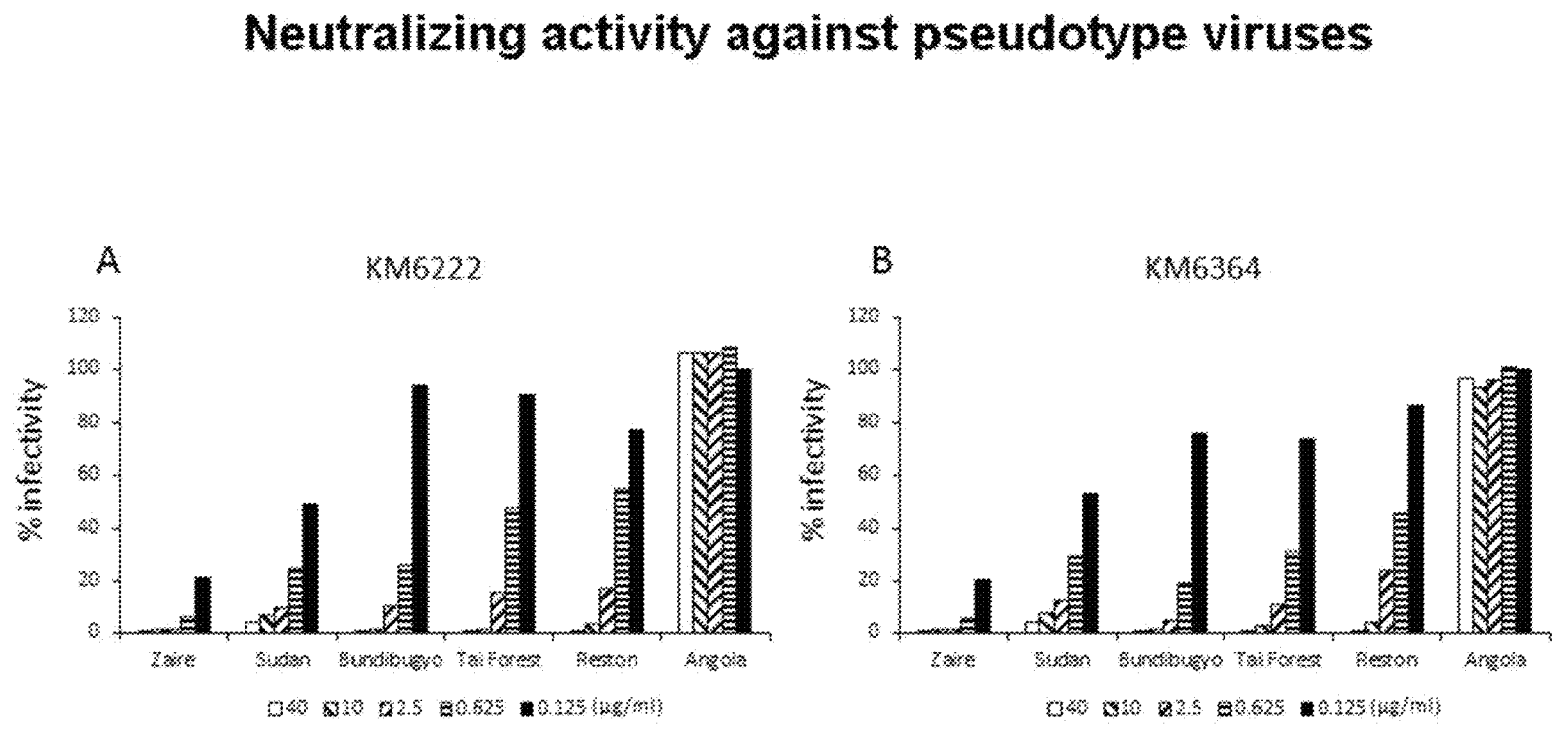

The results obtained are shown in FIG. 8. KM6364 (FIG. 8B) was shown to have the same neutralizing activity as KM6222 (FIG. 8A) against all pseudotype viruses of Zaire, Sudan, Bundibugyo, Tai Forest and Reston types. Moreover, the neutralizing activity of KM6364 was found to increase in a concentration-dependent manner against all the pseudotype viruses, as in the case of KM6222.

In Example 5, the 6D6 chimeric antibody KM6222 was shown to have the same neutralizing activity as the mouse monoclonal antibody 6D6. This indicates that the 6D6 chimeric antibody KM6364 with enhanced ADCC activity also has the same neutralizing activity as the mouse monoclonal antibody 6D6.

INDUSTRIAL APPLICABILITY

The present invention allows effective treatment and alleviation of infection with all species of ebolavirus.
Sequence Listing Free Text SEQ ID NO: 1 shows the amino acid sequence of a GP internal fusion loop of Zaire ebolavirus.

SEQ ID NO: 2 shows the amino acid sequence of a GP internal fusion loop of Sudan ebolavirus.

SEQ ID NO: 3 shows the amino acid sequence of a GP internal fusion loop of Bundibugyo ebolavirus.

SEQ ID NO: 4 shows the amino acid sequence of a GP internal fusion loop of Tai Forest ebolavirus.

SEQ ID NO: 5 shows the amino acid sequence of a GP internal fusion loop of Reston ebolavirus.

SEQ ID NO: 6 shows the amino acid sequence of an internal fusion loop of Zaire ebolavirus escape mutant strain [5/6].

SEQ ID NO: 7 shows the amino acid sequence of an internal fusion loop of Zaire ebolavirus escape mutant strain [1/6].

SEQ ID) NO: 8 shows the amino acid sequence of an internal fusion loop of Reston ebolavirus escape mutant strain [2/6].

SEQ ID NO: 9 shows the amino acid sequence of an internal fusion loop of Reston ebolavirus escape mutant strain [4/6].

SEQ ID NO: 10 shows the amino acid sequence of the light chain variable region of monoclonal antibody 6D6.

SEQ ID NO: 11 shows the amino acid sequence of the heavy chain variable region of monoclonal antibody 6D6.

SEQ ID NO: 12 shows the amino acid sequence of CDRL1 of monoclonal antibody 6D6.

SEQ ID NO: 13 shows the amino acid sequence of CDR12 of monoclonal antibody 6D6.

SEQ ID NO: 14 shows the amino acid sequence of CDRL3 of monoclonal antibody 6D6.

SEQ ID NO: 15 shows the amino acid sequence of CDRH1 of monoclonal antibody 6D6 according to the definition of Kabat.

SEQ ID NO: 16 shows the amino acid sequence of CDRH2 of monoclonal antibody 6D6 according to the definition of Kabat.

SEQ ID NO: 17 shows the amino acid sequence of CDRH3 of monoclonal antibody 6D6 according to the definition of Kabat.

SEQ ID NO: 18 shows the amino acid sequence of CDRH1 of monoclonal antibody 6D6 according to the definition of AbM.

SEQ ID NO: 19 shows the amino acid sequence of CDRH2 of monoclonal antibody 6D6 according to the definition of AbM.

SEQ ID NO: 20 shows the amino acid sequence of CDRH3 of monoclonal antibody 6D6 according to the definition of AbM.

SEQ ID NO: 21 shows the amino acid sequence of CDRH1 of monoclonal antibody 6D6 according to the definition of Chothia.

SEQ ID NO: 22 shows the amino acid sequence of CDRH2 of monoclonal antibody 6D6 according to the definition of Chothia.

SEQ ID NO: 23 shows the amino acid sequence of CDRH3 of monoclonal antibody 6D6 according to the definition of Chothia.

SEQ ID NO: 24 shows the amino acid sequence of the light chain of monoclonal antibody 6D6.

SEQ ID NO: 25 shows the amino acid sequence of the heavy chain of monoclonal antibody 6D6.

SEQ ID NO: 26 shows the nucleotide sequence of 6D6L-F1 primer.

SEQ ID NO: 27 shows the nucleotide sequence of 6D6L-R1 primer.

SEQ ID NO: 28 shows the nucleotide sequence of 6D6L-F2 primer.

SEQ ID NO: 29 shows the nucleotide sequence of 6D6L-R2 primer.

SEQ ID NO: 30 shows the nucleotide sequence of 6D6H-Avr-F primer.

SEQ ID NO: 31 shows the nucleotide sequence of 6D6H-Mut-Ala-R primer.

SEQ ID NO: 32 shows the nucleotide sequence of 6D6H-Mut-Ala-F primer.

SEQ ID NO: 33 shows the nucleotide sequence of 6D6H-Apa-R primer.

SEQ ID NO: 34 shows the nucleotide sequence of 6D6H-Mut-Ser-R primer.

SEQ ID NO: 35 shows the nucleotide sequence of 6D6H-Mut-Ser-F primer.

SEQ ID NO: 36 shows the amino acid sequence of a human antibody framework available for use as a framework material in the preparation of humanized antibody (light chain 1).

SEQ ID NO: 37 shows the amino acid sequence of a human antibody framework available for use as a framework material in the preparation of humanized antibody (light chain 2).

SEQ ID NO: 38 shows the amino acid sequence of a human antibody framework available for use as a framework material in the preparation of humanized antibody (heavy chain 1).

SEQ ID NO: 39 shows the amino acid sequence of a human antibody framework available for use as a framework material in the preparation of humanized antibody (heavy chain 2).

SEQ ID NO: 40 shows the amino acid sequence of H chain CDR3Ala.

SEQ ID NO: 41 shows the amino acid sequence of H chain CDR3Ser.

SEQ ID NO: 42 shows the amino acid sequence of the heavy chain variable region of 6D6 chimeric antibody (comprising Ser substituted for Cys in CDR3).

The invention claimed is:

1. A monoclonal antibody or an antigen-binding fragment thereof, which recognizes an internal fusion loop of the surface glycoprotein (GP) of ebolavirus and is capable of neutralizing the biological activity of ebolavirus, wherein the monoclonal antibody or the antigen-binding fragment thereof comprises:

(i) a light chain variable region comprising:
light chain CDR1 comprising the amino acid sequence of SEQ ID NO: 12,
light chain CDR2 comprising the amino acid sequence of SEQ ID NO: 13, and
light chain CDR3 comprising the amino acid sequence of SEQ ID NO: 14; and
a heavy chain variable region comprising: heavy chain CDR1 comprising the amino acid sequence of SEQ ID NO: 15,
heavy chain CDR2 comprising the amino acid sequence of SEQ ID NO: 16, and
heavy chain CDR3 comprising the amino acid sequence of SEQ ID NO: 17, or the amino acid sequence of SEQ ID NO: 17 comprising a substitution of one amino acid residue at position 7, wherein position 7 is substituted with alanine or serine; or (ii) a light chain variable region comprising:
light chain CDR1 comprising the amino acid sequence of SEQ ID NO: 12,
light chain CDR2 comprising the amino acid sequence of SEQ ID NO: 13, and
light chain CDR3 comprising the amino acid sequence of SEQ ID NO: 14; and
a heavy chain variable region comprising:
heavy chain CDR1 comprising the amino acid sequence of SEQ ID NO: 18,
heavy chain CDR2 comprising the amino acid sequence of SEQ ID NO: 19, and
heavy chain CDR3 comprising the amino acid sequence of SEQ ID NO: 20, or the amino acid sequence of SEQ ID NO: 20 comprising a substitution of one amino acid residue at position 7, wherein position 7 is substituted with alanine or serine; or (iii) a light chain variable region comprising:
light chain CDR1 comprising the amino acid sequence of SEQ ID NO: 12,
light chain CDR2 comprising the amino acid sequence of SEQ ID NO: 13, and
light chain CDR3 comprising the amino acid sequence of SEQ ID NO: 14; and
a heavy chain variable region comprising:
heavy chain CDR1 comprising the amino acid sequence of SEQ ID NO: 21,
heavy chain CDR2 comprising the amino acid sequence of SEQ ID NO: 22, and
heavy chain CDR3 comprising the amino acid sequence of SEQ ID NO: 23, or the amino acid sequence of SEQ ID NO: 23 comprising a substitution of one amino acid residue at position 7, wherein position 7 is substituted with alanine or serine.

2. The monoclonal antibody or antigen-binding fragment thereof according to claim 1, wherein the ebolavirus whose GP internal fusion loop is to be recognized comprises all of the following ebolaviruses: Zaire ebolavirus, Sudan ebolavirus, Bundibugyo ebolavirus, Reston ebolavirus and Tai Forest ebolavirus.

3. The monoclonal antibody or antigen-binding fragment thereof according to claim 2, wherein the monoclonal antibody or antigen-binding fragment thereof recognizes all GP internal fusion loops selected from the group consisting of SEQ ID NOs:1-5.

4. The monoclonal antibody or antigen-binding fragment thereof according to claim 1, selected from the group consisting of:
a monoclonal antibody which comprises a light chain variable region comprising light chain CDR1 comprising the amino acid sequence of SEQ ID NO: 12, light chain CDR2 comprising the amino acid sequence of SEQ ID NO: 13, and light chain CDR3 comprising the amino acid sequence of SEQ ID NO: 14, and
a heavy chain variable region comprising heavy chain CDR1 comprising the amino acid sequence of SEQ ID NO: 15, heavy chain CDR2 comprising the amino acid sequence of SEQ ID NO: 16, and heavy chain CDR3 comprising the amino acid sequence of SEQ ID NO: 17;
a monoclonal antibody which comprises a light chain variable region comprising light chain CDR1 comprising the amino acid sequence of SEQ ID NO: 12, light chain CDR2 comprising the amino acid sequence of SEQ ID NO: 13, and light chain CDR3 comprising the amino acid sequence of SEQ ID NO: 14, and
a heavy chain variable region comprising heavy chain CDR1 comprising the amino acid sequence of SEQ ID NO: 15, heavy chain CDR2 comprising the amino acid sequence of SEQ ID NO: 16, and heavy chain CDR3 comprising the amino acid sequence of SEQ ID NO: 40; and a monoclonal antibody which comprises a light chain variable region comprising light chain CDR1 comprising the amino acid sequence of SEQ ID NO: 12, light chain CDR2 comprising the amino acid sequence of SEQ ID NO: 13, and light chain CDR3 comprising the amino acid sequence of SEQ ID NO: 14, and a heavy chain variable region comprising heavy chain CDR1 comprising the amino acid sequence of SEQ ID NO: 15, heavy chain CDR2 comprising the amino acid sequence of SEQ ID NO: 16, and heavy chain CDR3 comprising the amino acid sequence of SEQ ID NO: 41.

5. The monoclonal antibody or antigen-binding fragment thereof according to claim 1, selected from the group consisting of:

a monoclonal antibody which comprises a light chain variable region comprising light chain CDR1 comprising the amino acid sequence of SEQ ID NO: 12, light chain CDR2 comprising the amino acid sequence of SEQ ID NO: 13, and light chain CDR3 comprising the amino acid sequence of SEQ ID NO: 14, and a heavy chain variable region comprising heavy chain CDR1 comprising the amino acid sequence of SEQ ID NO: 18, heavy chain CDR2 comprising the amino acid sequence of SEQ ID NO: 19, and heavy chain CDR3 comprising the amino acid sequence of SEQ ID NO: 20;

a monoclonal antibody which comprises a light chain variable region comprising light chain CDR1 comprising the amino acid sequence of SEQ ID NO: 12, light chain CDR2 comprising the amino acid sequence of SEQ ID NO: 13, and light chain CDR3 comprising the amino acid sequence of SEQ ID NO: 14, and a heavy chain variable region comprising heavy chain CDR1 comprising the amino acid sequence of SEQ ID NO: 18, heavy chain CDR2 comprising the amino acid sequence of SEQ ID NO: 19, and heavy chain CDR3 comprising the amino acid sequence of SEQ ID NO: 40; and a monoclonal antibody which comprises a light chain variable region comprising light chain CDR1 comprising the amino acid sequence of SEQ ID NO: 12, light chain CDR2 comprising the amino acid sequence of SEQ ID NO: 13, and light chain CDR3 comprising the amino acid sequence of SEQ ID NO: 14, and a heavy chain variable region comprising heavy chain CDR1 comprising the amino acid sequence of SEQ ID NO: 18, heavy chain CDR2 comprising the amino acid sequence of SEQ ID NO: 19, and heavy chain CDR3 comprising the amino acid sequence of SEQ ID NO: 41.

6. The monoclonal antibody or antigen-binding fragment thereof according to claim 1, selected from the group consisting of:

a monoclonal antibody which comprises a light chain variable region comprising light chain CDR1 comprising the amino acid sequence of SEQ ID NO: 12, light chain CDR2 comprising the amino acid sequence of SEQ ID NO: 13, and light chain CDR3 comprising the amino acid sequence of SEQ ID NO: 14, and a heavy chain variable region comprising heavy chain CDR1 comprising the amino acid sequence of SEQ ID NO: 21, heavy chain CDR2 comprising the amino acid sequence of SEQ ID NO: 22, and heavy chain CDR3 comprising the amino acid sequence of SEQ ID NO: 23;

a monoclonal antibody which comprises a light chain variable region comprising light chain CDR1 comprising the amino acid sequence of SEQ ID NO: 12, light chain CDR2 comprising the amino acid sequence of SEQ ID NO: 13, and light chain CDR3 comprising the amino acid sequence of SEQ ID NO: 14, and a heavy chain variable region comprising heavy chain CDR1 comprising the amino acid sequence of SEQ ID NO: 21, heavy chain CDR2 comprising the amino acid sequence of SEQ ID NO: 22, and heavy chain CDR3 comprising the amino acid sequence of SEQ ID NO: 40; and a monoclonal antibody which comprises a light chain variable region comprising light chain CDR1 comprising the amino acid sequence of SEQ ID NO: 12, light chain CDR2 comprising the amino acid sequence of SEQ ID NO: 13, and light chain CDR3 comprising the amino acid sequence of SEQ ID NO: 14, and a heavy chain variable region comprising heavy chain CDR1 comprising the amino acid sequence of SEQ ID NO: 21, heavy chain CDR2 comprising the amino acid sequence of SEQ ID NO: 22, and heavy chain CDR3 comprising the amino acid sequence of SEQ ID NO: 41.

7. The monoclonal antibody or antigen-binding fragment thereof according to claim 1, which comprises:

a light chain variable region comprising the amino acid sequence of SEQ ID NO: 10; and a heavy chain variable region comprising the amino acid sequence of SEQ ID NO: 11, or the amino acid sequence of SEQ ID NO: 11 comprising substitution of one amino acid residue at position 105, wherein position 105 is substituted with alanine or serine.

8. The monoclonal antibody or antigen-binding fragment thereof according to claim 7, which comprises:

a light chain variable region consisting of the amino acid sequence of SEQ ID NO: 10; and a heavy chain variable region consisting of the amino acid sequence of SEQ ID NO: 11.

9. The monoclonal antibody or antigen-binding fragment thereof according to claim 1, which is a chimeric antibody or a humanized antibody.

10. The monoclonal antibody or antigen-binding fragment thereof according to claim 1, which has antibody-dependent cell-mediated cytotoxicity.

11. An isolated nucleic acid molecule, which encodes the monoclonal antibody or antigen-binding fragment thereof according to claim 1.

12. An expression vector, which comprises the nucleic acid molecule according to claim 11.

13. A hybridoma cell or a transformed cell, which comprises the nucleic acid molecule according to claim 11.

14. A method of detecting ebolavirus, comprising
reacting the monoclonal antibody or antigen-binding fragment thereof according to claim 1 with a biological sample; and
detecting signals from the reacted antibody.

15. A pharmaceutical composition, which comprises the monoclonal antibody or antigen-binding fragment thereof according to claim 1 and a pharmacologically acceptable carrier, diluent or excipient.

16. A method of inhibiting Ebola virus, comprising administering the monoclonal antibody or antigen-binding fragment thereof according to claim 1 in an effective amount to a subject in need thereof.

17. A method for producing the antibody or antigen-binding fragment thereof according to claim 1, which comprises the steps of culturing the hybridoma or transformed cell which comprises a nucleic acid molecule encoding the monoclonal antibody or antigen-binding fragment thereof in a medium to produce and accumulate the antibody in the culture supernatant, and collecting and purifying the antibody.

* * * * *